United States Patent
Lepulu et al.

(10) Patent No.: US 6,533,770 B1
(45) Date of Patent: Mar. 18, 2003

(54) CANNULA AND METHOD OF MANUFACTURE AND USE

(75) Inventors: Keke J. Lepulu, Menlo Park; Sylvia W. Fan, San Francisco, both of CA (US)

(73) Assignee: Heartport, Inc., Redwood City, CA (US)

( * ) Notice: Subject to any disclaimer, the term of this patent is extended or adjusted under 35 U.S.C. 154(b) by 0 days.

(21) Appl. No.: 09/010,296

(22) Filed: Jan. 21, 1998

(51) Int. Cl.⁷ ............................................. A61M 25/00
(52) U.S. Cl. ..................... 604/524; 604/523; 604/525; 604/264; 604/526
(58) Field of Search .................. 604/264, 273, 604/523, 524, 525, 526, 527, 6, 16; 138/123, 124, 125, 127, 129, 132, 133, 134, 138, 144

(56) References Cited

U.S. PATENT DOCUMENTS

| | | | |
|---|---|---|---|
| 3,416,531 A | | 12/1968 | Edwards |
| 3,592,184 A | | 7/1971 | Watkins et al. |
| 3,757,768 A | * | 9/1973 | Kline .......................... 128/2 M |
| 3,995,623 A | | 12/1976 | Blake et al. |
| 4,004,299 A | | 1/1977 | Runge |
| 4,044,765 A | * | 8/1977 | Kline ............................. 128/2 |
| 4,058,857 A | | 11/1977 | Runge et al. |
| 4,080,958 A | | 3/1978 | Bregman et al. |
| 4,129,129 A | | 12/1978 | Amrine |
| 4,639,252 A | * | 1/1987 | Kelly et al. .................. 604/523 |
| 4,721,115 A | * | 1/1988 | Owens ........................ 604/523 |
| 4,808,163 A | | 2/1989 | Laub |
| 4,856,529 A | | 8/1989 | Segal |
| 4,862,874 A | | 9/1989 | Kellner |
| 4,889,137 A | | 12/1989 | Kolobow |
| 4,943,275 A | | 7/1990 | Stricker |
| 4,985,014 A | | 1/1991 | Orejola |

(List continued on next page.)

FOREIGN PATENT DOCUMENTS

| | | |
|---|---|---|
| WO | WO 95/12421 | 5/1995 |
| WO | WO 96/38194 | 12/1996 |

OTHER PUBLICATIONS

American Edwards Laboratories, Edslab, *Thermodilution and Monitoring Catheters*, Instruction pamphlet, no date.
Bourassa, "Cardiovascular Catheters, Sterile," USCI, A Division of C.R. Bard, Inc., Rev. 6–72/5070017.

(List continued on next page.)

*Primary Examiner*—Brian L. Casler
*Assistant Examiner*—Cris L. Rodriguez

(57) ABSTRACT

A cannula having reinforced sections and nonreinforced sections, the nonreinforced sections having openings communicating with the lumen of the cannula. The nonreinforced sections are plain tubing and the reinforced sections are formed by winding a coated elongate member in a helical manner around a mandrel. The coated elongate member preferably has a square cross-sectional shape so that adjacent portions of the coated elongate member engage one another when the coated elongate member is wound around the mandrel. The coated elongate member is then heated so that the coating on adjacent portions of the coated elongate member fuse together to form an integral structure. Another layer of material may be provided on the radially inner or outer wall of the coated elongate member. The resulting tubular body is reinforced by the elongate member which is encased in the fused coating. The tubular body is cut into sections which are fused to the plain tubing sections to form the cannula. The reinforced sections and the plain tubing sections are alternately disposed along all or a portion of the length of the cannula. The openings are formed in the plain tubing sections for withdrawing or delivering fluid into or out of the lumen of the cannula.

14 Claims, 20 Drawing Sheets

U.S. PATENT DOCUMENTS

| | | | | |
|---|---|---|---|---|
| 4,990,143 A | * | 2/1991 | Sheridan | 604/523 |
| 5,011,469 A | * | 4/1991 | Buckberg et al. | 604/4 |
| 5,013,296 A | * | 5/1991 | Buckberg et al. | 604/44 |
| 5,021,045 A | | 6/1991 | Buckberg et al. | |
| 5,033,998 A | | 7/1991 | Corday et al. | |
| 5,053,008 A | | 10/1991 | Bajaj | |
| 5,102,390 A | | 4/1992 | Crittenden et al. | |
| 5,207,228 A | | 5/1993 | Roelandt et al. | |
| 5,269,752 A | | 12/1993 | Bennet | |
| 5,312,344 A | | 5/1994 | Grinfeld et al. | |
| 5,370,618 A | | 12/1994 | Leonhardt | |
| 5,410,797 A | | 5/1995 | Rupp | |
| 5,433,700 A | | 7/1995 | Peters | |
| 5,443,074 A | | 8/1995 | Roelandt et al. | |
| 5,458,574 A | | 10/1995 | Machold et al. | |
| 5,476,450 A | | 12/1995 | Ruggio | |
| 5,509,897 A | | 4/1996 | Twardowski et al. | |
| 5,522,961 A | | 6/1996 | Leonhardt | |
| 5,527,292 A | | 6/1996 | Thome | |
| 5,545,138 A | | 8/1996 | Fugoso | |
| 5,569,184 A | | 10/1996 | Chum | |
| 5,573,520 A | * | 11/1996 | Schwartz et al. | 604/523 |
| 5,584,803 A | | 12/1996 | Stevens et al. | |
| 5,584,821 A | * | 12/1996 | Hobbs et al. | 604/523 |
| 5,688,245 A | | 11/1997 | Runge | |
| 5,769,828 A | * | 6/1998 | Jonkman | 604/280 |

OTHER PUBLICATIONS

Breyer et al., "Is a Left Ventricular Vent Necessary for Coronary Artery Bypass Operations Perfomed with Cardioplegic Arrest?" *J Thorac Card Surg*, 1983;86:338–349.

Chellappan et al., "Gravity Venting of the Left Ventricle: A useful adjunct," *J Extra–Corp Tech*, 1994;26(1):34–36.

DLP Product Catalog, Third Edition, Cardiac Vents and Sumps, 1993, p. 35.

Heimbecker et al., "A New Approach to Left Heart Decompression," *Ann Thorac Surg*, 1976;21:456–457.

Laughlin et al., "Left Heart Decompression via the Pulmonary Artery," *Thorac Card Surg*, 1983;31:117–118.

Little et al., "Use of the Pulmonary Artery for Left Ventricular Venting During Cardic Operations," *J Thorac Card Surg*, 1984;87:532–538.

Medtronic Bio–Medicus, Inc., Bio–Medicus Cannula Instructions for Use Manual, Sterile and Non–Pyrogenic Single–Use Only, PN 85281 Rev C (10–91).

Orejola et al., The Internal Ventricular Venting Loop Catheter. A New, Simplified, Single, Single Cannulation Approach for a Ventricular Assist System, *ASIAO Journal*, 1994, pp. 181–185.

Roberts et al., "Relative Efficacy of Left Ventricular Venting and Venous Drainage Techniques Commonly Used During Coronary Artery Bypass Graft Surgury," *Ann Thorac Sur*, 1983;36:444–452.

Schneider et al., "A Technique for Cardioplegic Infusion and Left Heart Venting During Coronary Artery Bypass Grafting," *Ann Thorac Surg*, 1983;36:105–106.

Shaw et al., "Venticular Apical Vents and Postoperative Focal Contraction Abnormalities in Patients Unergoing Coronary Artery Bypass Surgery," *Circulation*1977;55:434–438.

Stassano et al., "False Aneurysm from the Aortic Vent Site," *J Card Surg*, 1982;23:401–402.

Vucins et al., "Vent Stitch Entrapment of Swan–Ganz Catheters During Cardiac Surgery," *Anesth Analg*, 1984;63:772–774.

Webster Laboratories, Webster Laboratories Electrode Catherter—Deflectable Tip, Product Information, Innovations in Electophysiology, M–5276–04C.

DLP, Inc. Worldwide Medical Innovations Product Catalog, $3^{rd}$ Edition Pulmonary Artery Vent Cannula, Product No. 12004.

World Medical Manufacturing Corporation, Polycath brochure, 1996.

European Search Report 99903149.5–2305–US9900998 mailed Aug. 28, 2001.

* cited by examiner

CANNULA AND METHOD OF MANUFACTURE AND USE

BACKGROUND OF THE INVENTION

The present invention is directed to reinforced hollow tubes and their methods of manufacture and use. A specific application of the present invention is for arterial and venous cardiopulmonary bypass cannula. The present invention is particularly useful as the arterial return cannula or the venous withdrawal cannula for the cardiopulmonary bypass (CPB) system described in U.S. Pat. No. 5,584,803, the subject matter of which is incorporated herein by reference. The CPB system has an arterial cannula which is used to return oxygenated blood to the patient's vascular system, and a venous cannula which is used to withdraw venous blood from the patient's vascular system. An aortic occlusion catheter passes through the arterial cannula. The aortic occlusion catheter is used to block blood flow through the ascending aorta and deliver cardioplegic fluid to arrest the heart for performing surgery on the heart and great vessels. The aortic occlusion catheter is inserted through the same lumen in the arterial cannula which is used to return arterial blood to the patient so that the arterial blood essentially passes in the annular space between the aortic occlusion catheter and the arterial return cannula.

An advantage of the CPB system described above is that only one opening in the patient's arterial system is required for both delivery of cardioplegic fluid and return of arterial blood. In order to achieve optimum blood and cardioplegic fluid flow rates, the wall of the arterial cannula must be minimized while retaining enough structural integrity to prevent kinking and/or cracking. The present invention is particularly useful in providing a thin walled cannula which may be used as an arterial return cannula for the system described above.

A known method of making a reinforced cannula is to dip a mandrel in a polymer solution and wrap a metal wire over the polymer. The mandrel is then dipped again to encase the metal wire between two layers of polymer.

Another known method of making a reinforced cannula is to extrude a polymer tubing, wrap a metal wire around the polymer tubing, and extrude another polymer layer over the metal wire.

A problem with the known methods of manufacturing a reinforced cannula is that the spacing between adjacent wires must be relatively large to ensure that the polymer flows between adjacent coils so that the two polymer layers bond together to form an integrated structure. Unfortunately, the relatively large spacing requires a relatively thick polymer layer to provide the necessary strength since the wire has a large pitch. The relatively thick polymer layer is also required to ensure that a sufficient amount of polymer is provided to fill the relatively large space. The resulting cannula therefore has a relatively thick wall.

Accordingly, there is a need in the art for an improved method of manufacturing reinforced tubing and, in particular, cannulae for venous withdrawal and arterial return of blood for use with a cardiopulmonary bypass system.

SUMMARY OF THE INVENTION

The present invention provides a cannula with at least a portion of its length reinforced, as well as a method of manufacturing the cannula.

According to one aspect of the invention, an elongate member, such as a steel or polymer wire, is coated with a coating, preferably a polymer, thereby forming a coated elongate member. A preferred method of coating the material is to coextrude the material over the elongate member. The coated elongate member is then wound helically around a mandrel and heated so that the coating on adjacent parts of the elongate member bond together. The coated elongate member is then mounted to a cannula body.

In one preferred embodiment, the coated elongate member is formed so that opposing sides of the coated elongate member engage one another when the coated elongate member is wrapped around the mandrel. A preferred cross-sectional shape is substantially square. An advantage of the present invention is that the coating does not need to flow between adjacent portions of the helically-wound member since the coated elongate members are configured to have sides which engage one another. In another aspect of the invention, the coated elongate member is compressed after being wound around the mandrel. The coated elongate member is preferably compressed with a heat shrink tube placed over the coated elongate member before heating. The shrink tube compresses the polymer to further ensure bonding between adjacent portions of the coated elongate member.

In a more specific preferred embodiment, a layer is positioned over and/or below the coated elongate member. The layer is preferably positioned over the coated elongate member and is applied as a tube of material having a larger inner diameter than the largest outer diameter of the coated elongate member. The tube is expanded, preferably by inflating the tube, and the coated elongate member is positioned inside the tube. The tube is then deflated so that it contracts around the coated elongate member. The tube and coated elongate member are then heated to fuse the elongate member and tube together to form an integrated structure. Although it is preferred to apply the layer as a tube, the layer may also be applied by dipping the coated elongated member in a suitable solution.

An advantage of a cannula constructed according to this aspect of the invention is that the cannula has a thin-walled construction while providing a lumen having a relatively large inner diameter. The lumen is particularly suited to receive an aortic occlusion catheter while still providing enough annular area between the catheter and lumen wall for return of arterial blood to sustain full CPB.

According to another aspect of the invention, a cannula is constructed so as to include reinforced sections and nonreinforced sections and a lumen passing through the sections. The respective sections are preferably alternately disposed along a portion or all of the length of the cannula. For example, a distal portion of the cannula may include alternating reinforced and nonreinforced sections, while the remaining length of the cannula is reinforced. Alternatively, the proximal and distal portions of the cannula may include alternating reinforced and non-reinforced sections, while the cannula is reinforced between these portions. As another alternative, the entire length of the cannula may include alternating reinforced and nonreinforced sections.

The reinforced sections of the cannula comprise tubular sections which include a reinforcing member while the nonreinforced sections comprise tubular sections which are substantially free of the reinforcing member. One or more openings are formed in the nonreinforced sections and serve as entry or exit ports for fluid being withdrawn from or delivered to a patient's vascular system. For example, the cannula may be used to withdraw venous blood from a patient's vascular system which is delivered to and oxygenated by a cardiopulmonary bypass system. In addition, or alternatively, the cannula may be used to deliver oxygenated blood from the cardiopulmonary bypass system to the patient's vascular system.

In one preferred embodiment, the reinforced sections of the cannula comprise a reinforcing member encased in a material, while the nonreinforced sections of the cannula comprise plain tubing sections. As an example, the reinforcing member may be elongate stainless steel wire, while the material encasing the wire is a suitable polymer.

According to this aspect of the invention, a method of making a cannula for withdrawing fluid from or delivering fluid to a patient's vascular system is also provided. In a preferred embodiment, the method comprises steps of forming a reinforced tubular body comprising a reinforcing member, and separating the reinforced tubular body to form a plurality of separate reinforced tubular sections each of which comprises the reinforcing member. A tubular section which is substantially free of the reinforcing member is disposed between at least two of the reinforced tubular sections, and the sections are bonded together to form a cannula having separate reinforced sections and a lumen extending therethrough. At least one opening is formed in the cannula between the reinforced sections such that fluid can flow through the opening and the lumen of the cannula.

In yet another aspect of the invention, a cannula comprises a tubular body having one or more openings disposed at one or more locations which are proximal to a midpoint of the cannula, the openings passing through the cannula so as to communicate with a lumen extending through the cannula. The openings are configured to allow fluid to pass into or out of the cannula along a proximal portion thereof, as opposed to only a distal portion thereof, as is conventional. When the cannula is used as a venous withdrawal or arterial return cannula for a CPB system, some of the blood being passed into or out of the cannula enters the proximal openings. As a result, it is not necessary to deliver all of the blood between the CPB system and the distal portion or end of the cannula, thereby allowing reduced pressure differentials to drive fluid flow, as compared with conventional cannulae. In one preferred embodiment, the cannula includes reinforced and nonreinforced sections, and the openings are formed in the nonreinforced sections.

BRIEF DESCRIPTION OF THE DRAWINGS

These and other aspects, benefits, features and advantages of the invention will become apparent with the following description of preferred embodiments, wherein.

DETAILED DESCRIPTION OF PREFERRED EMBODIMENTS

Figure 1:
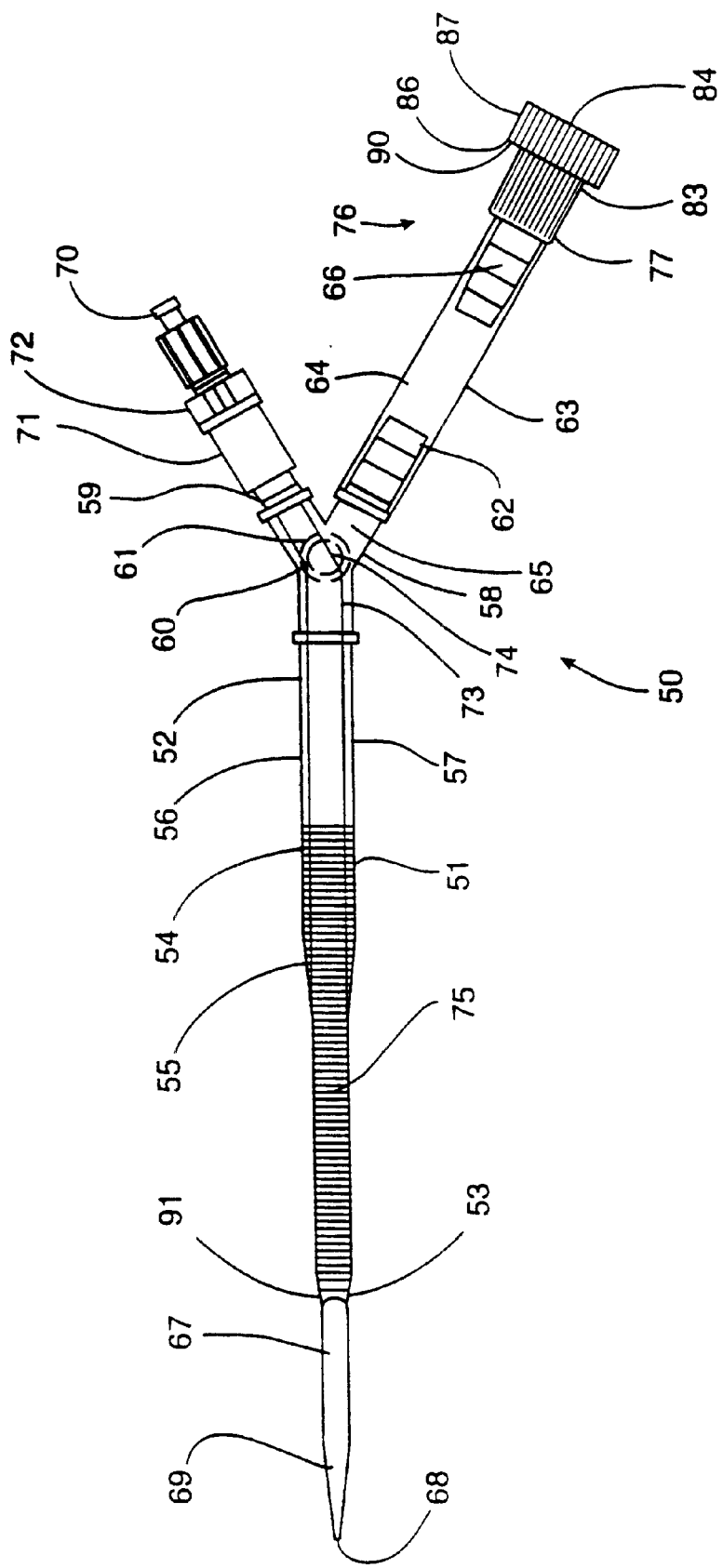
FIG. 1 is a front view of an arterial cannula and introducer sheath for use with an endoaortic occlusion catheter.
Figure 2:
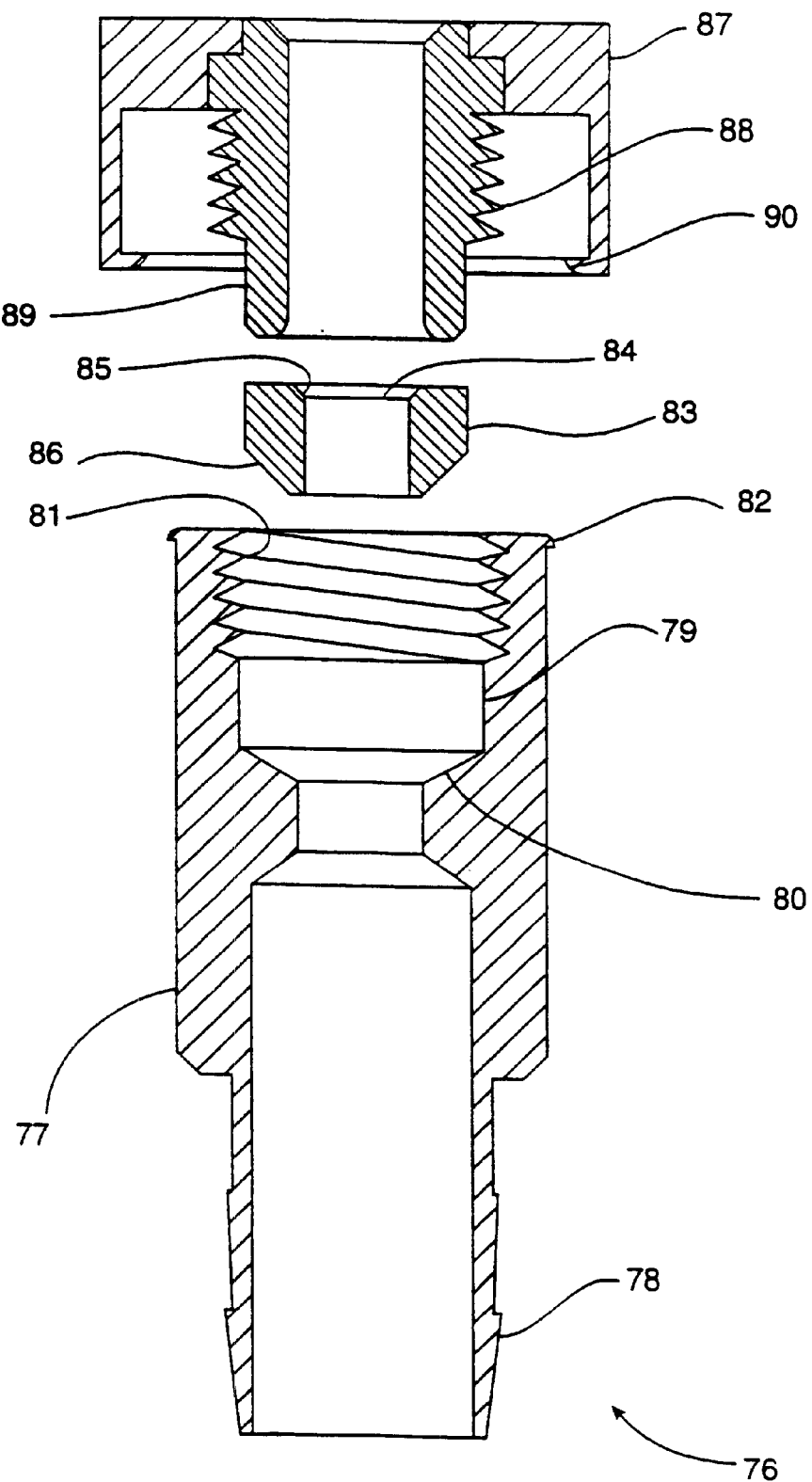
FIG. 2 is a cross sectional view of a hemostasis fitting for the arterial cannula and introducer sheath of FIG. 1.

The invention is directed to cannulae and their methods of manufacture. A particularly useful application of the present invention is for arterial and venous cardiopulmonary bypass cannulae.

Referring to FIGS. 1–4, an endoaortic occlusion catheter 95 is coupled to a cannula 50 that is configured to serve as an arterial bypass cannula and an introducer sheath for introduction of the endoaortic occlusion catheter 95. By configuring the catheter 95 and cannula 50 in this manner, both devices are inserted through the same arterial opening which minimizes trauma to the patient. Use of the cannula 50 to receive an aortic occlusion catheter is merely an example of one possible use of the present invention, and it will be appreciated that the cannula 50 may be used for other purposes. Furthermore, the term cannula as used herein refers to any hollow body structure, such as a catheter or trocar, which is inserted into a patient's vascular system. The cannula 50 is coupled to a CPB system (not shown in FIGS. 1–4) for delivering oxygenated blood to the patient's arterial system. The aortic occlusion catheter 95 has a lumen which is coupled to a source of cardioplegic fluid (not shown in FIGS. 1–4). The lumen is coupled to an outlet which is distal to the balloon 96. Cardioplegic fluid is delivered through the lumen and outlet for arresting a patient's heart when the patient is on full cardiopulmonary bypass. The balloon 96 occludes the ascending aorta to prevent oxygenated blood from reaching the coronary arteries and starting the heart prematurely.

The cannula 50 has a body 51 which is preferably made of a transparent, flexible, biocompatible polyurethane elastomer or similar material. In one preferred embodiment, the body 51 has a 45° beveled distal end 53, a proximal end 52, a blood flow lumen 57 extending between the proximal end 52 and the distal end 53, and an outflow port 91 at the distal end 53. Alternatively, the body 51 can have a straight cut distal end with a chamfered or rounded edge. Optionally, a plurality of additional outflow ports may be provided along the length of body 51, particularly near distal end 53. The body 51 is tapered from the proximal end 52 to the distal end 53 and, in one preferred embodiment, is reinforced with a coil of flat stainless steel wire 54 embedded in the wall of the body 51. Adjacent to the proximal end 52 of the body 51, proximal to the reinforcing coil 54, is a clamp site which is a flexible section of the body 5 1 that can be clamped with an external clamp, such as a Vorse type tube occluding clamp, to form a hemostatic seal to temporarily stop blood flow through the lumen 57 of the cannula 50.

In a preferred embodiment, the body 51 has a length between about 10 cm and 60 cm, and preferably between about 12 cm and 30 cm. In one particular embodiment, the body 51 has a distal external diameter of approximately 7 mm or 21 French (Charriere scale) and a distal internal diameter of approximately 6.0 mm or 18 French. In a second particular embodiment, the body 51 has a distal external diameter of approximately 7.7 mm or 23 French (Charriere scale) and a distal internal diameter of approximately 6.7 mm or 20 French. Preferably, in either embodiment, the proximal end 52 of the body 51 of has an internal diameter of approximately ⅜ inch or 9.5 mm. The choice of which embodiment of the cannula 50 to use for a given patient will depend on the size of the patient and the diameter of the artery (or vein) chosen for cannulation. Generally, patients with a larger body mass will require a higher infusion rate of oxygenated blood while on cardiopulmonary bypass, therefore the larger arterial bypass cannula 50 should be chosen if the size of the artery allows. While the illustrated and preferred embodiments of the cannulae of the invention have a circular or substantially circular cross-section, and thus preferred sizes are provided in the form of diameters, it will be appreciated that any other cannula shape or configuration may be used.

An adapter assembly 65 is connected to the proximal end 52 of the body 51. In one preferred embodiment, the adapter assembly 65 and the body 51 are supplied preassembled as a single, sterile, ready-to-use unit. Alternatively, the adapter assembly 65 can be packaged and sold as a separate unit to be connected to the body 51 at the point of use. The adapter assembly 65 has a Y-fitting 58 which is connected to the proximal end 52 of the cannula body 51. The Y-fitting 58 has a first branch ending in a barbed connector 59 which is configured for fluid connection to tubing 92 (FIG. 4) from a cardiopulmonary bypass system. To prepare the arterial bypass cannula 50 for insertion into a peripheral artery, such as a patient's femoral artery or brachial artery, by an arterial cutdown or by a percutaneous Seldinger technique, a connector plug 71, which is molded of a soft, elastomeric material, is placed over the barbed connector 59. A tapered dilator 67 is passed through a wiper-type hemostasis seal 72 in the connector plug 71. The wiper-type hemostasis seal 72 is a hole through the elastomeric connector plug 71 that has a slight interference fit with the external diameter of the dilator 67. A series of ridges can be molded within the hemostasis seal 72 to reduce the sliding friction on the dilator 67 while maintaining a hemostatic seal. It is understood that any other type of hemostasis seal 72 may be used with the present invention.

The dilator 67 has a tapered distal tip 69, a proximal hub 70 with a luer lock connector, and a guidewire lumen 79, sized for an 0.038 inch diameter guidewire, that runs from the distal tip 69 to the proximal hub 70. The diameter of the dilator 67 is such that the dilator 67 substantially fills the cannula lumen 57 at the distal end 53 of the cannula body 51. The length of the dilator 67 is such that the distal tip 69 of the dilator 67 extends approximately 2 to 5 cm, and more preferably 4 to 5 cm, beyond the beveled end 53 of the body 51 when the dilator hub 70 is against the connector plug 71. The dilator 67 may assume a bend 73 in it at the point where the dilator 67 passes through the Y-fitting 58 when the dilator 67 is fully inserted. One or more depth markers 74, 75 can be printed on the dilator 67 with a nontoxic, biocompatible ink. One depth marker 74 may be placed so that, when the marker 74 is just proximal to the hemostasis seal 72 on the elastomeric connector plug 71, the tapered distal tip 69 of the dilator 67 is just emerging from the beveled end 53 of the body 51. In one particular embodiment, the tapered dilator 67 is made of extruded polyurethane with a radiopaque filler so that the position of the dilator can be verified fluoroscopically.

Figure 3:
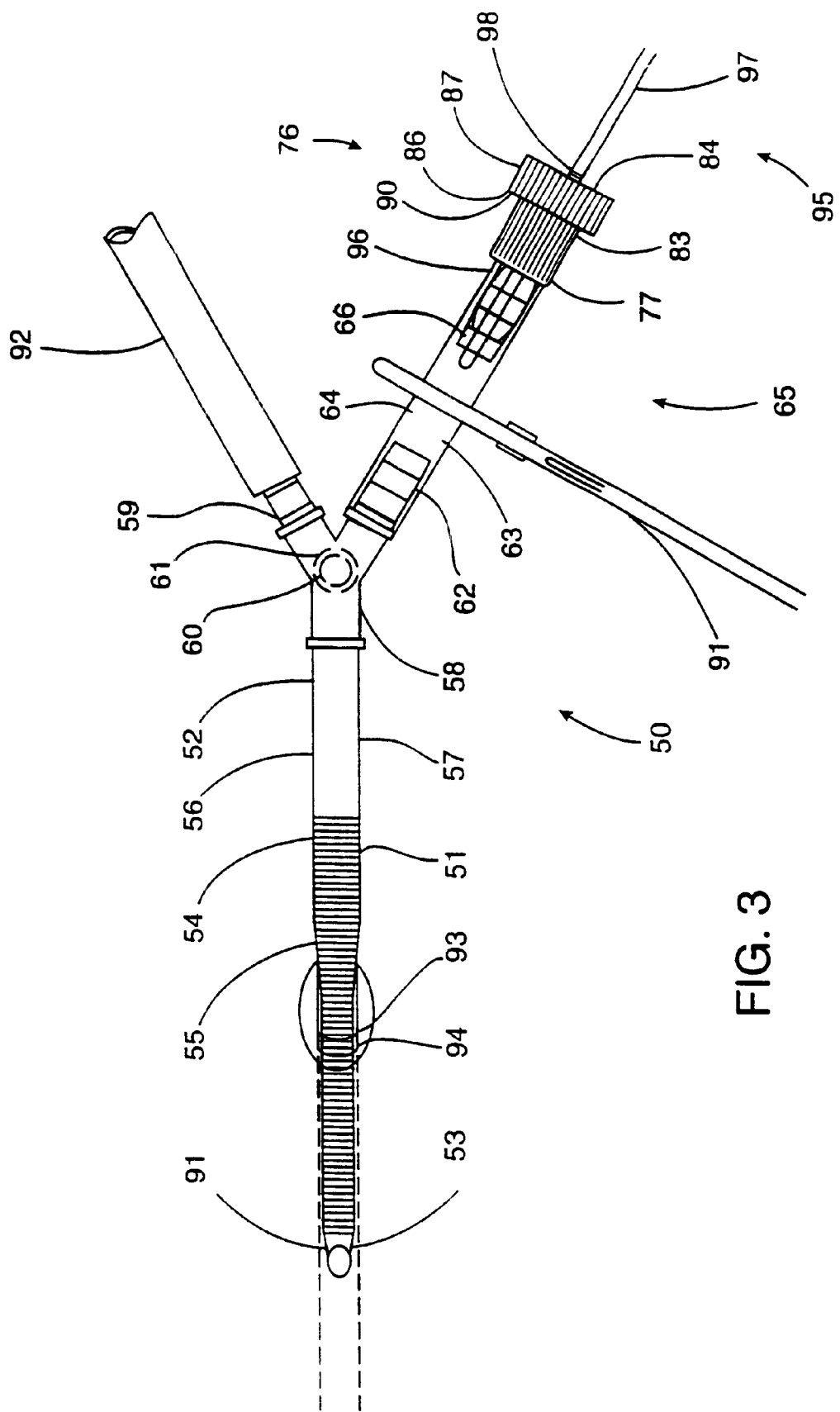
FIG. 3 illustrates the cannula of FIG. I with the endoaortic occlusion catheter introduced into the catheter insertion chamber.
Figure 4:
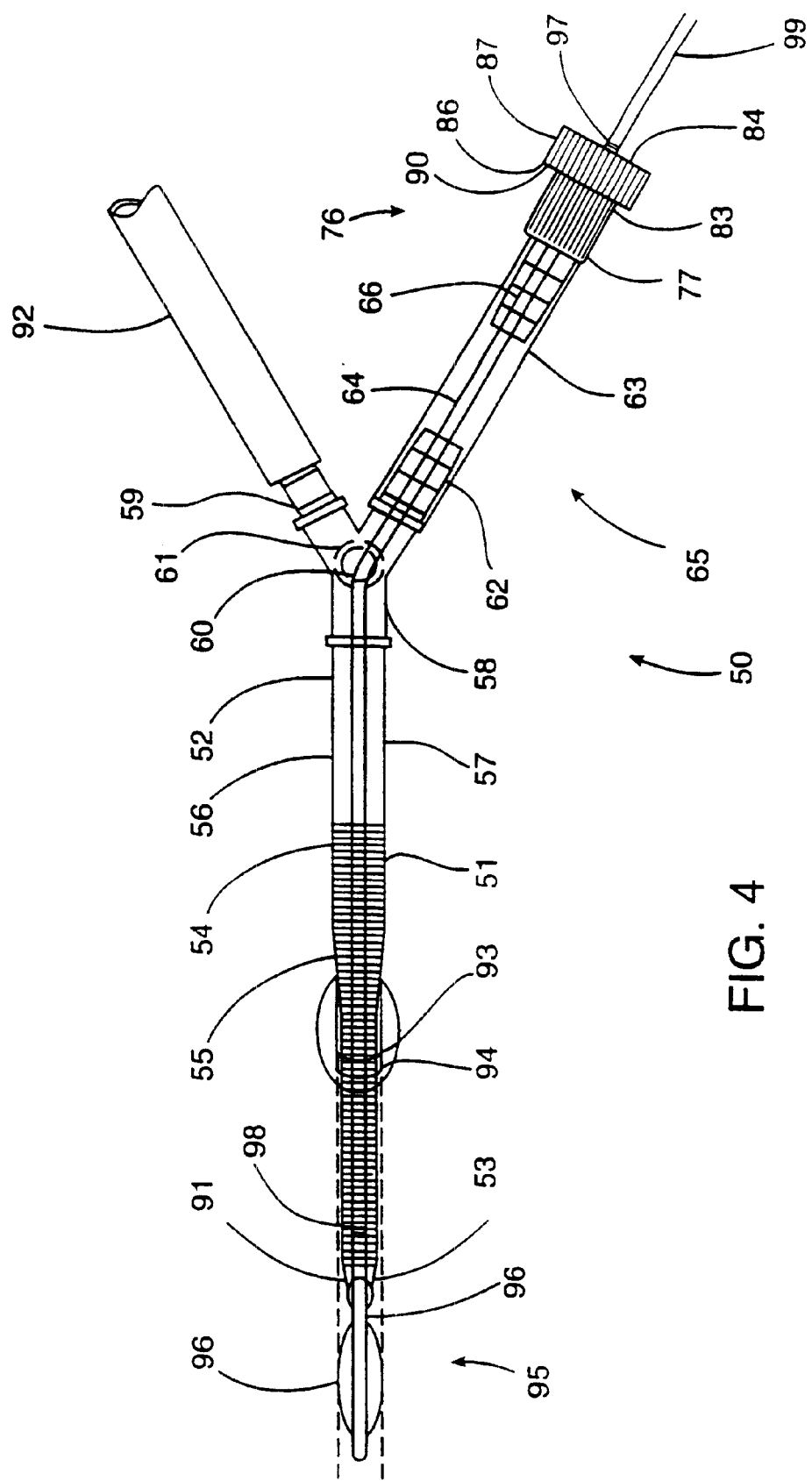
FIG. 4 illustrates the cannula of FIGS. 1 and 2 with the endoaortic occlusion catheter introduced into the patient's femoral artery.

A second branch of the Y-fitting 58 is connected to an extension tube 62 which terminates in a hemostasis valve 76 configured to receive the endoaortic occlusion catheter 95 therethrough (FIGS. 3 and 4). The extension tube 62 has a flexible middle section which serves as a proximal clamp site 64 that can be clamped with an external clamp, such as a Vorse type tube occluding clamp, to form a hemostatic seal to temporarily stop blood flow through the lumen 63 of the extension tube 62. The lumen 63 of the extension tube 62 between the proximal clamp site 64 and the hemostasis valve 76 serves as a catheter insertion chamber 66, the function of which will be more fully explained in connection with FIG. 3. The hemostatic seal may, of course, be any other type of seal.

In a preferred embodiment of the arterial bypass cannula 50, the hemostasis valve 76 is a type of compression fitting known in the industry as a Tuohy-Borst adapter, however, any other suitable seal may be used. The adapter 76 is shown in greater detail in FIG. 2. The adapter 76 has a compressible tubular or ring-shaped elastomeric seal 83 that fits within a counterbore 79 in the fitting body 77. The elastomeric seal 83 is preferably made from a soft, resilient, self-lubricating elastomeric material, such as silicone rubber having a hardness of approximately 20–50 and preferably 40–50 Shore A durometer. The elastomeric seal 83 has a central passage 84 with a beveled entry 85 on the proximal end of the passage 84. The elastomeric seal 83 has a beveled distal surface 86 angled at about 45° which fits against a tapered seat 80 in the bottom of the counterbore 79 that is angled at about 60°. A threaded compression cap 87 screws onto the fitting body 77. The threaded cap 87 has a tubular extension 89 which fits within the counterbore 79 in the fitting body 77. An externally threaded section 88 on the proximal end of the tubular extension 87 engages an internally threaded section 81 within the proximal end of the counterbore 79. When the threaded cap 87 is screwed down onto the fitting body 77, the tubular extension 89 bears on the elastomeric seal 83 forcing it against the tapered seat 80 of the counterbore 79. The resultant force on the elastomeric seal 83 squeezes the elastomeric seal 83 inward to close off the passage 84 to make a hemostatic seal. When the threaded cap 87 is unscrewed again from the fitting body 77, the central passage 84 of the elastomeric seal 83 opens up again. The deliberate 15° mismatch between the angle of the beveled distal surface 86 of the elastomeric seal 83 and the tapered seat 80 of the counterbore 79 prevents the elastomeric seal 83 from binding and causes the passage 84 to open up reliably when the threaded cap 87 is unscrewed from the fitting body 87. An internal ridge 90 within the threaded cap 87 engages in a snap fit with an external ridge 82 on the proximal end of the fitting body 77 to keep the threaded cap 87 from being inadvertently separated from the fitting body 77 if the threaded cap 87 is unscrewed to the point where the threads 88, 81 are no longer engaged.

In one particular embodiment, the central passage 84 of the elastomeric seal 83 has an internal diameter of about 5 mm to allow clearance for inserting a catheter 95 with a shaft diameter of 3–4 mm through the adapter 76 without damaging the occlusion balloon 96 mounted on it. The adapter 76 is adjustable through a range of positions, including a fully open position for inserting the balloon catheter 96, a partially closed position for creating a sliding hemostatic seal against the shaft 97 of the catheter 95, and a completely closed position for creating a hemostatic seal with no catheter in the passage 84. In an alternative embodiment, the passage 84 of the elastomeric seal 83 can be sized to have a slight interference fit with the shaft 97 of the catheter 95 when uncompressed. In this embodiment, the adapter 76 has positions which include a fully open position for creating a sliding hemostatic seal against the shaft 97 of the catheter 95, and a completely closed position for creating a hemostatic seal with no catheter in the passage 84. In a second alternative embodiment, a separate ring-like wiper seal (not shown) is added in series with the adapter 76 to create a passive sliding hemostatic seal against the shaft 97 of the catheter 95 without the necessity of tightening the threaded cap 87. Additionally, the adapter 76, in either embodiment, may have a tightly closed position for securing the catheter shaft 97 with respect to the patient. In other alternative embodiments, other known hemostasis valves may be substituted for the Tuohy-Borst adapter 76 as just described.

In a particularly preferred embodiment, the internal surface of the lumen 63 of the extension tube 62 and/or the internal surface of the lumen 57 of the body 51 are coated with a highly lubricious biocompatible coating, such as polyvinyl pyrrolidone, to ease the passage of the endoaortic occlusion catheter 95, and especially the occlusion balloon 96, through these lumens. Other commercially available lubricious biocompatible coatings can also be used, such as Photo-Link™ coating available from BSI Surface Modification Services of Eden Prairie, Minn.; sodium hyaluronate coating available from Biocoat of Fort Washington, Pa.; proprietary silicone coatings available from TUA of Sarasota, Fla.; and fluid silicone or silicon dispersions. Similarly, a distal portion of the exterior of the body 51 can be coated with one of these lubricious biocompatible coatings to facilitate insertion of the arterial bypass cannula 50 into the artery at the cannulation site. Furthermore, the endoaortic occlusion catheter 95 itself, in any of the embodiments described herein, can be coated with one of these lubricious biocompatible coatings to facilitate its insertion and passage through the arterial bypass cannula 50 and the patient's vasculature. Preferably, the occlusion balloon 96 of the endoaortic occlusion catheter 95 should be free of any lubricious coating so that there is sufficient friction between the expanded occlusion balloon and the interior of the aortic wall to prevent accidental dislodgement or migration of the occlusion balloon 96.

In operation, the arterial bypass cannula 50 is prepared for insertion as shown in FIG. 1, with the tapered dilator 67 in place in the blood flow lumen 57 of the body 51 and with the fitting 76 completely closed. An arterial cutdown is made into an artery, preferably the patient's femoral artery, although the subclavian or a radial artery could be used. The cutdown is made at the cannulation site or a guidewire is placed percutaneously using the Seldinger technique and the dilator 67 and the distal end 53 of the body 51 are inserted into the lumen of the artery with the bevel facing up. A suture 94 can be tied around the artery 93 where the body 51, as shown in FIG. 3, is inserted to avoid bleeding from the artery 93 at the cannulation site. The dilator 67 is then withdrawn from the body 51, allowing blood to flash back and fill the lumen 57 of the body 51. When the tip 68 of the dilator 67 is proximal to the distal clamp site 56 an external clamp is applied to the distal clamp site 56 to stop further blood flow. The dilator 67 is completely withdrawn and the connector plug 71 is removed so that a tube 92 from the cardiopulmonary bypass system can be attached to the barbed connector 59 of the Y-fitting 58, as shown in FIG. 3. Air is bled from the arterial bypass cannula 50 by elevating the extension tube 62 and opening the fitting 76 slightly and releasing the external clamp on the distal clamp site 56 to allow the blood to flow out through the fitting 76. Alternatively, air can be bled out of the arterial bypass cannula 50 through an optional vent fitting with a luer cap (not shown) that can be provided on the Y-fitting 58 or an infusion line and a three-way stopcock. The optional vent fitting can be also used as a port for monitoring perfusion pressure within the arterial bypass cannula 50. Once the air is bled out of the system, the external clamp can be removed from the distal clamp site 56 and the CPB system pump can be turned on to perfuse the patient's arterial system with oxygenated blood at a rate of about 3 to 6 liters/minute, preferably at a pump pressure of less than about 500 mm Hg.

To introduce the endoaortic occlusion catheter 95 into the arterial bypass cannula 50, an external clamp 91 is placed on the proximal clamp site 64, as shown in FIG. 3, to stop blood from flowing out through the extension tube 62 and the adapter 76 is opened all the way by unscrewing the threaded cap 87 to open up the passage 84 through the elastomeric seal 83. The distal end of the endoaortic occlusion catheter 95 with the occlusion balloon 96 mounted thereon is inserted through the passage 84 of the adapter 76 into the insertion chamber 66 of the arterial bypass cannula 50. Optionally, first and second depth markers 98, 99 may be printed on the shaft 97 of the endoaortic occlusion catheter 95 with a nontoxic, biocompatible ink. The first depth marker 98 on the catheter 95 indicates when the occlusion balloon 96 is entirely distal to the elastomeric seal 83. When the first depth marker 98 is positioned just proximal to the threaded cap 87, the adapter 76 should be tightened to create a sliding, hemostatic seal around the catheter shaft 97. Now, the clamp 91 can be removed to allow the catheter 95 to be advanced distally through the arterial bypass cannula 50.

Before the endoaortic occlusion catheter 95 enters the blood flow lumen 57 within the Y-fitting 58, the perfusion rate from the cardiopulmonary bypass system pump should be temporarily turned down to a rate of about 1 to 2 liters/minute to avoid hemolysis, tubing disruptions or other complications due to the additional flow resistance caused by the occlusion balloon 96 as it passes through the blood flow lumen 57. The catheter 95 can now be advanced distally until the occlusion balloon 96 is distal to the distal end 53 of the body 51. A second depth marker 99 on the catheter 95 indicates when the occlusion balloon 96 is entirely distal to the distal end 53 of the body 51. When the second depth marker 99 reaches the proximal end of the threaded cap 87, as shown in FIG. 3, the perfusion rate from the cardiopulmonary bypass system pump should be returned to a rate of about 3 to 6 liters/minute. The endoaortic occlusion catheter 95 can now be advanced into the ascending aorta for partitioning the heart and inducing cardioplegic arrest according to the methods described above. When the endoaortic occlusion catheter 95 is in position within the ascending aorta the adapter 76 can be tightened around the catheter 95 to act as a friction lock to hold the catheter in place.

After completion of the surgical procedure on the heart, the endoaortic occlusion catheter 95 can be removed from the cannula 50 by reversing the sequence of operations described above. The cannula 50 can remain in place until the patient has been weaned from cardiopulmonary bypass, then the cannula 50 can be removed and the arterial puncture site repaired.

It should be noted that for the venous side of the cardiopulmonary bypass system, a similar dual purpose venous bypass cannula and introducer sheath with the above-described features can be used for accessing any vein, such as the femoral, jugular or subclavian vein, for example, to introduce a venting catheter or other devices into the venous side of the circulatory system. In a venous configuration the dual purpose venous bypass cannula and introducer sheath preferably has an external diameter of about 21 to 32 French units, an internal diameter of about 18 to 30 French units, and a length of about 50 to 75 cm.

Figure 5:
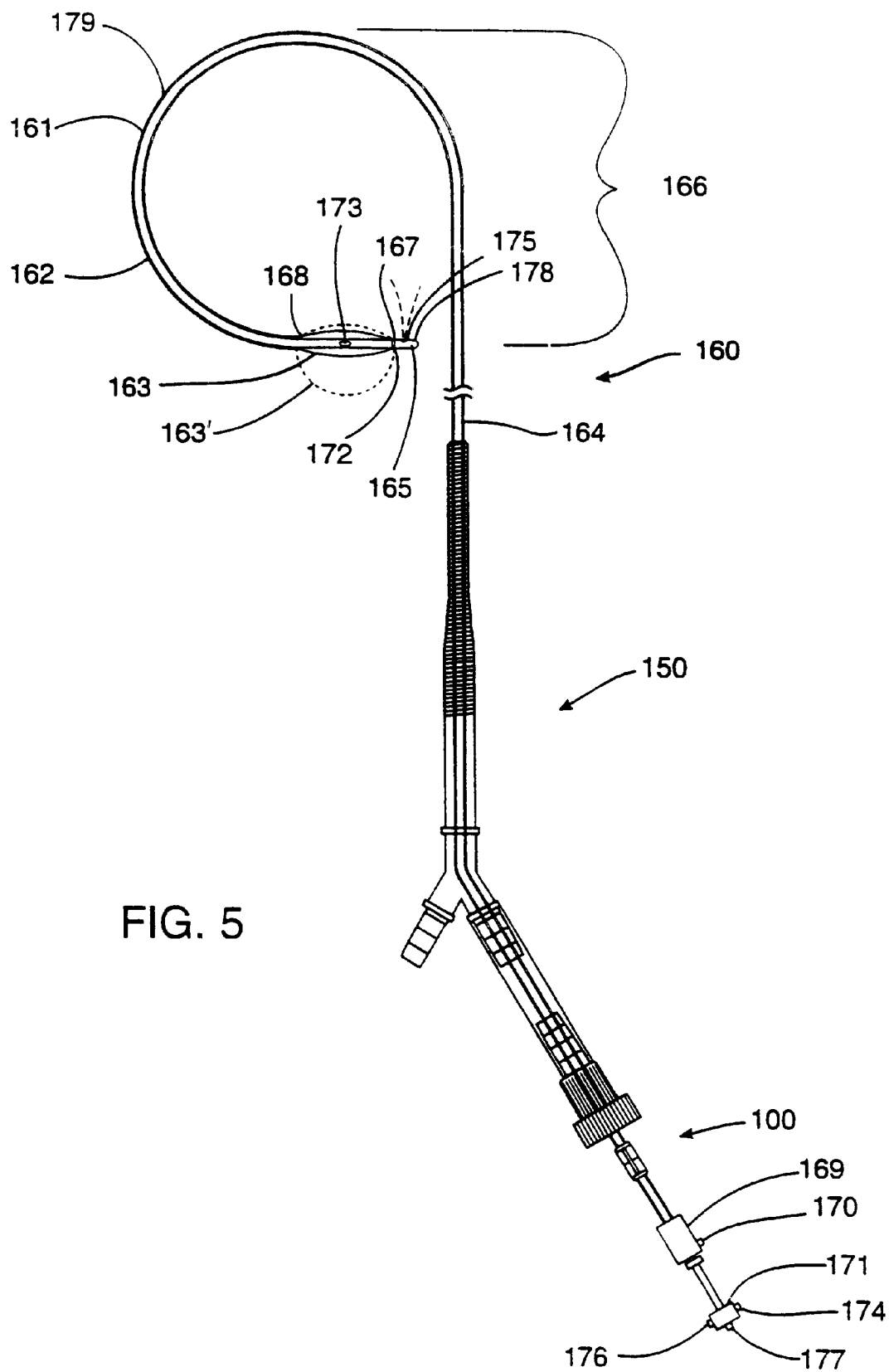
FIG. 5 illustrates a multifunction embodiment of the endoaortic occlusion catheter combined with the arterial cannula and introducer sheath.

It should be noted that while several aspects of the present invention have been illustrated and discussed separately in the foregoing description, many of these aspects can be advantageously combined into a single, multifunction embodiment. As an illustrative example, FIG. 5 shows a multifunction embodiment of the endoaortic occlusion catheter 160 combining several of the inventive aspects previously discussed. As discussed above, however, any other aortic occlusion catheter may be used and preferred aortic occlusion catheters are described in co-pending U.S. patent application Ser. No. 08/692,992. The shaft 164 of the catheter 160 has a coaxial construction with an inner 161 and outer 162 tubular member. The shaft 164 may be made with varying degrees of stiffness along the length of the shaft 164, culminating in a soft atraumatic tip 165 which may be highly loaded with a radiopaque filler. The shaft 164 may be made with a precurved distal portion 166 or with a precurved distal portion 166 which is out of plane with the proximal portion of the shaft 164. An expandable occlusion balloon 163 is mounted on the distal portion 166 of the shaft 164. The balloon 163 preferably has a low profile deflated state with an ellipsoidal shape. In addition, the balloon 163 may have an eccentric or asymmetrical inflated profile 163' which would also provide a steering means for the distal tip of the catheter.

The occlusion balloon 163 is mounted with its distal balloon neck 167 attached to the inner tubular member 161 and its proximal balloon neck attached to the outer tubular member 162. The inner tubular member 161 is attached at its proximal end to a first hub 171 and the outer tubular member 162 is attached at its proximal end to a second hub 169 which are axially slidably and/or rotatable with respect to one another. An infusion fitting 177, such as a luer lock, on the first hub 171 is connected to an infusion lumen 178 which terminates at the distal end of the catheter 160. An inflation fitting 170, preferably a luer lock, on the second hub 169 is connected to an inflation lumen 179 defined by an annular space between the inner 161 and outer 162 tubular members which communicates with the interior of the occlusion balloon 163.

The second hub 169 may be moved proximal and/or rotated with respect to the first hub 171 to minimize the deflated profile of the occlusion balloon 163. The lower deflated profile of the occlusion balloon 163 facilitates easy insertion of the catheter 160 through a dual function arterial cannula and introducer sheath 50. When the endoaortic occlusion catheter 160 is combined with the dual function arterial cannula and introducer sheath 50, the shaft 164 of the catheter 160 should be made with an additional 20–25 cm of length for a total shaft length of approximately 100–115 cm. The diameter of the catheter shaft 164 should also be minimized as much as possible to reduce the amount of cross sectional area the catheter shaft 164 takes up in the blood flow lumen of the arterial cannula 50. To this end, this combined embodiment is made with a distal pressure transducer 172 and a balloon pressure monitoring transducer 173 mounted on the inner tubular member 161. The distal pressure transducer 172 and the balloon pressure monitoring transducer 173 are electrically connected to an electrical connector 174 on the first hub 171. Also on the first hub 171 is a fiberoptic connector 176 which connects to a fiberoptic bundle 175 which terminates with a means for directing a lateral beam of light at the distal end of the catheter 160 for aortic transillumination and/or for facilitating nonfluoroscopic placement of the catheter 160. The fiberoptic bundle 175 may also be made as a separate unit for insertion through the infusion lumen 178 of the catheter 160 to further reduce the catheter shaft diameter while maintaining maximum functionality. The diameter of the catheter shaft 164 can thus be reduced to as small as 8 to 10.5 French (2.7–3.5 mm diameter).

Figure 6:
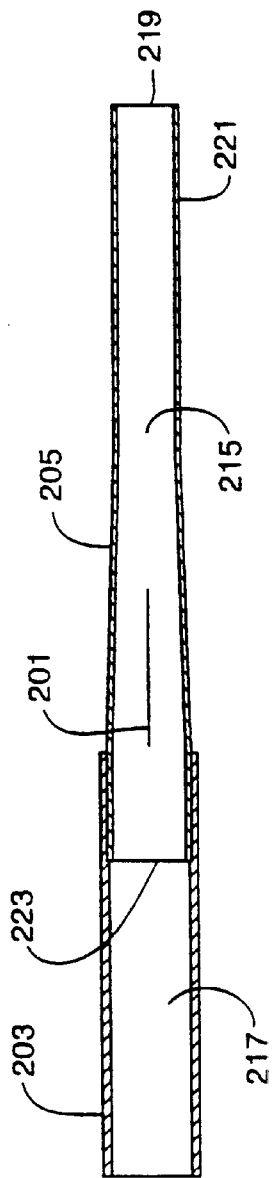
FIG. 6 is a cross-sectional view of a cannula having a reinforced section coupled to a body.

Referring to FIG. 6, a cross-sectional view of another preferred cannula 201 is shown. A specific application of the present invention is for arterial and venous cannulae for a cardiopulmonary bypass system. The methods and devices described herein in connection with arresting a patient's heart and placing the patient on cardiopulmonary bypass are incorporated here for use with the cannula 201 described below and any other cannula described herein. The cannula 201 includes a body 203 and a reinforced section 205. As will be discussed in greater detail below, the reinforced section 205 has a thin wall which maximizes the lumen size for a given outer diameter.

Figure 7:
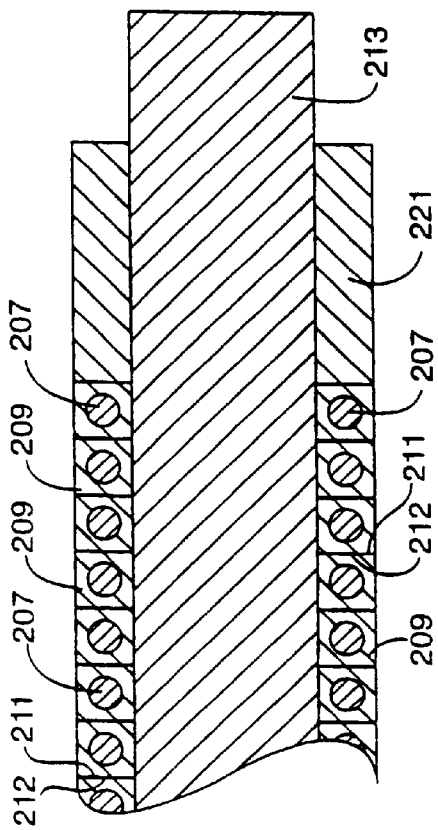
FIG. 7 is a cross-sectional view of a coated elongate member wrapped around a mandrel.

Referring to FIG. 7, an apparatus for forming the reinforced section 205 is shown. The reinforced section 205 of the cannula 201 is preferably manufactured with an elongate member 207 coated with a coating 209. The elongate member 207 may be made of any suitable material which has the requisite structural characteristics such as stainless steel, nickel titanium, or a polymer. A preferred material is 304V stainless steel wire having a 0.008 inch diameter. The elongate member 207 may have any cross-sectional shape and a preferred shape is circular.

The elongate member 207 is preferably coated with the coating 209 by coextruding the elongate member and the coating 209. Any suitable coating 209 may be used and preferred coatings include polymers and specifically polyurethane, PVC, polyether block amide which can be purchased from Elf Atochem Inc. under the name PEBAX, and styrene block copolymer which can be purchased from Shell under the name KRATON. A preferred polyurethane is polytetramethylene glycol ether which can be purchased from Dow under the name Dow 2363 PELLETHANE 80AE.

The coating 209 is extruded over the elongate member 207 so that the coating 209 has opposing sides 211, 212 which are configured to engage one another when the coated elongate member 207 is wrapped around a mandrel 213. A preferred shape is a quadrangle, and specifically a square, however, any other shape may be used including irregular shapes so long as the opposing sides 211, 212 are configured to engage one another. The square cross-sectional shape preferably has sides having lengths between 0.010 and 0.020 inch and more preferably between 0.010 and 0.015 inch and most preferably 0.014 inch. The relative dimensions for the thickness of the cannula have been exaggerated as compared to the inner diameter for clarity with the actual dimensions being provided herein.

The coated elongate member 207 is wrapped around the mandrel 213 in a helical shape. The mandrel 213 is preferably coated with a lubricious coating such as TFE to prevent sticking. An advantage of the present invention over other methods of forming a cannula is that the coating 209 encasing the reinforcing member 207 does not have to flow between adjacent portions of the elongate member 207 since the elongate member 207 is coextruded to have a shape in which the opposing sides 211, 212 already engage one another. A shrink tube (not shown), preferably a heat shrink tube such as a polyester or fluorinated ethylene propylene (FEP) tube, may also be positioned around the elongate member 207 to facilitate bonding. The shrink tube is preferably removed after heating. The wound coated elongate member 207 may also be dipped in a polymer solution such as polyurethane and tetrahydrofuran (solvent) to enhance the structural characteristics of the reinforced section 205. Furthermore, the coating or tube may also be applied over the wound coated elongate member. Alternatively, a tube may be positioned over the mandrel 213 and the coated elongate member 207 may be wound over the tube. The reinforced section 205 may be made of more than one layer of the coated elongate member 207 and the coated elongate member 207 may be wrapped in different directions to increase the hoop and tensile strength. Although it is preferred that the elongate member 207 has a constant cross-sectional profile, the elongate member 207 may also have differing sizes to provide stiff and flexible areas.

After the coated elongate member 207 has been wrapped around the mandrel 213, the coated elongate member 207 is heated to melt the coating 209 and fuse adjacent portions of the coating 209 together to form an integrated structure. The coated elongate member 207 is preferably heated using an oven; however, any other heating method may be used including an IR lamp, heating the mandrel 213, or a combination thereof. The coated elongate member 207 is then cooled and removed from the mandrel 213 thereby forming the reinforced section 205 of the cannula 201.

Figure 8:
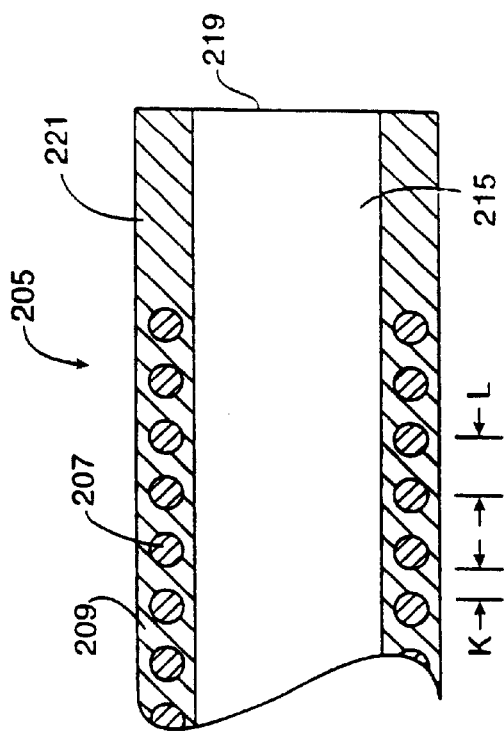
FIG. 8 is a cross-sectional view of the coated elongate member of FIG. 7 after heating and removal from the mandrel.

Referring to FIG. 8, the resulting reinforced section 205 is shown. The coating 209 on the elongate member 207 fuses together so that the coating 209 forms a matrix which is reinforced by the elongate member 207. Although it is preferred to heat the coated elongate member 207 to fuse the material together, the coated elongate member may also be coated with a solvent before winding the coated elongate member around the mandrel. The solvent would fuse the adjacent material together and would flash off leaving the fused material.

Referring again to the cross-section of FIG. 6, the reinforced section 205 has a lumen 215 therethrough for delivering or withdrawing fluids to or from a patient. The reinforced section 205 is attached to the body 203 by any method and is preferably bonded to the body 203 by insert molding. The body 203 includes a lumen 217 which is fluidly coupled to the lumen 215 of the reinforced section 205. The body 203 has been simplified and may include valves, a Y-connector, luer connections or any other features. Furthermore, the body 203 is preferably configured to engage a 3/8 inch fitting which is a standard size for CPB systems. The lumen 215 of the reinforced section 205 may be any size but preferably has an internal diameter of at least 0.180, more preferably at least 0.236, and most preferably at least 0.242, but no more than 0.375 inch.

A distal end 219 of the cannula 201 has an atraumatic tip 221 for introduction into the patient. The atraumatic tip 221 is preferably an integral extension of the coating 209 (FIG. 8) extending beyond the reinforced section 205. The atraumatic tip 221 has a length of at least 0.050 inch and a thickness adjacent to the reinforced section which is preferably the same as the reinforced section.

A proximal end 223 of the reinforced section 205 is flared outward slightly so that the proximal end 223 has a larger lumen than the distal end 219. The proximal end 223 preferably forms an angle of between 2° and 10° and more preferably between 4° and 6° with respect to a longitudinal axis of the cannula 201.

The cannula 201 is particularly useful for arterial return and venous drainage cannulae for the CPB system described above since the cannula 201 can be manufactured with a thin wall. As such, the reinforced section 205 preferably has a thickness between 0.010 and 0.025 inch, more preferably between 0.013 and 0.020 inch, and most preferably between 0.014 and 0.017 inch. The preferred thickness provides the necessary structural characteristics while maximizing the lumen size so that flow rates through the cannula are optimized. The cannula 201 of the present invention also has a unique spacing between adjacent portions of the coated elongate member. Referring to FIG. 8, a gap K between adjacent portions of the elongate member 207 is preferably less than 0.019 inch, more preferably less than 0.006 inch, and most preferably less than 0.004 inch. A centerline spacing L between adjacent portions of the elongate member 207 is preferably less than 0.022 inch, more preferably less than 0.018 inch, and most preferably less than 0.014 inch.

Figure 9:
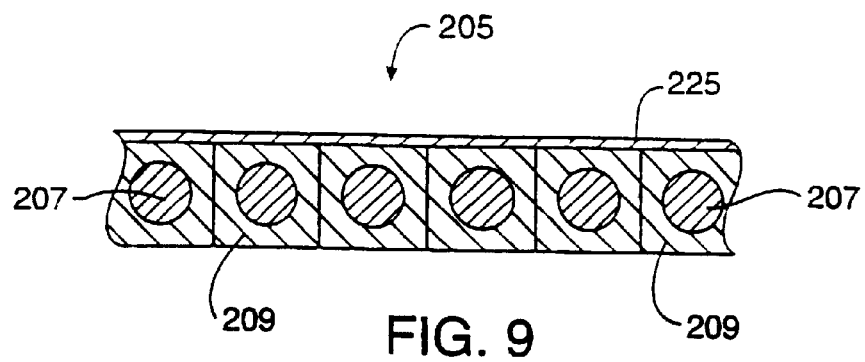
FIG. 9 is a cross-sectional view of a second construction for the reinforced section.

Referring to FIG. 9, a second preferred construction is shown for the reinforced section 205. The elongate member 207 and coating 209 are preferably the same as described above in connection with FIGS. 7–8, however, another layer 225 is positioned either over the elongate member 207 or below the elongate member 207 to increase the strength of the reinforced section 205. When the layer 225 is on the radially inner wall of the cannula 201, the layer 225 may be applied by dipping the mandrel 213 in a suitable solution, extruding the layer over the mandrel 213, or positioning a tube over the mandrel 213. The coated elongate member 207 is then wrapped around the mandrel 213 and heated to fuse the coating 209 and layer 225 together. When the layer 225 is on the radially outer wall of the cannula, the layer 225 may be applied by dipping the coated elongate member 207 in a suitable solution after wrapping the coated elongate member 207 around the mandrel 213, extruding the layer 225 over the coated elongate member 207 wound around the mandrel 213, or positioning a tube over the coated elongate member wound around the mandrel 213 and fusing it to the coated elongate member. The coated elongate member 207 and coating 209 have the same preferred dimensions described above. The layer 225 has thickness of no more than 0.007 inch, more preferably between 0.001 and 0.003 inch, and is preferably made of the same materials as the coating 209 described above. FIG. 9 depicts the reinforced section 205 before heating; however, after heating the polymer layer 225 and coating 209 fuse together to form an integrated structure.

Figure 10:
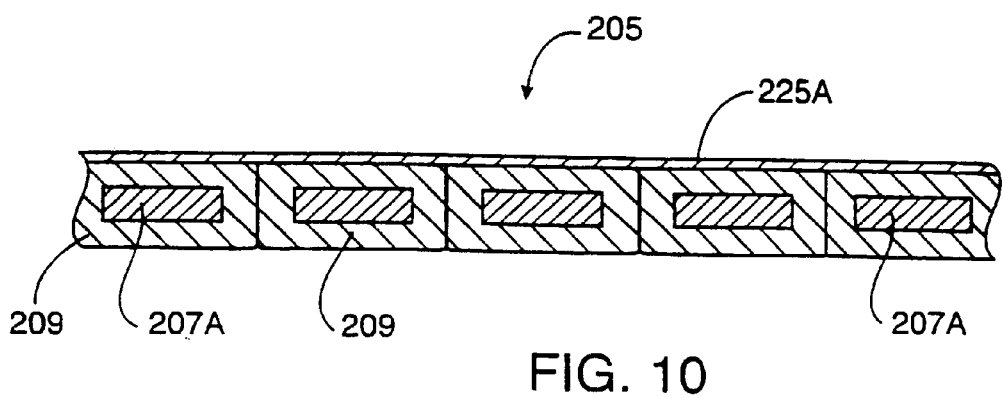
FIG. 10 is a cross-sectional view of a third construction for the reinforced section.

Referring to FIG. 10, a third preferred construction for the reinforced section 205 is shown. The reinforced section 205 is made according to the same procedure described above except that a different elongate member 207A is used. The elongate member 207A is preferably made of metal and has a quadrangle shaped cross-section. A preferred elongate member is a stainless steel flat wire having cross-sectional dimensions of 0.005 inch by 0.020 inch. The elongate member 207A is preferably coextruded with the coating 209 to a thickness of 0.003 all around, although any thickness may be used. A layer 225A, which is preferably the same as the layer 225 described above, may be positioned on the radially inner or outer wall of the cannula. The resulting structure yields an inner diameter of at least 0.180 inch, more preferably at least 0.236 inch, and most preferably at least 0.242 inch and no more than 0.375 inch. The resulting reinforced section 205 has a thickness of 0.011 inch without the layer 225A and 0.013 inch with the layer 225A. The reinforced section 205 may also be formed without the layer 225A so that the wall thickness of the cannula is minimized. FIG. 10 depicts the reinforced section 205 before heating; however, after heating the layer 225A and coating 209 fuse together to form an integrated structure.

Figure 11:
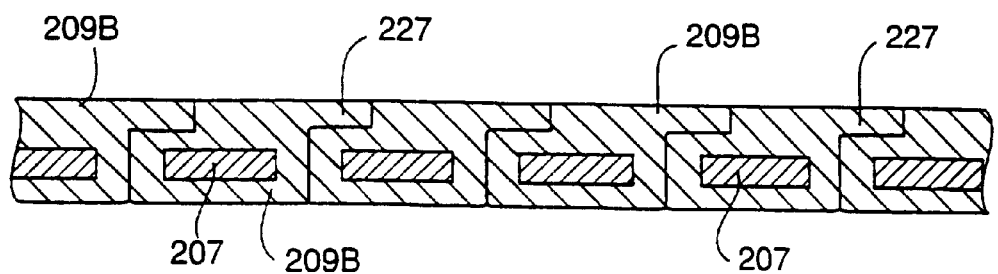
FIG. 11 is a cross-sectional view of a fourth construction for the reinforced section.

Referring to FIG. 11, a fourth preferred construction for the reinforced section 205 is shown. The reinforced section 205 is made according to the same procedure described above and has the same elongate member 207 as described in connection with FIG. 10. The coating 209B has an overlapping portion 227 which lies over an adjacent portion of the coated elongate member 207. The elongate member 207 is a 0.005 inch by 0.020 inch stainless steel flat wire, and the coating has a width of 0.003 inch all around the elongate member 207. The overlapping portion 227 has a thickness of 0.005 inch and a length of 0.013 inch. The overlapping portion 227 provides an interlocking relationship between adjacent portions of the coated elongate member 207. FIG. 11 depicts the reinforced section 205 before heating; however, after heating the material from adjacent portions of the coating 209 and the overlapping portion 227 fuse together to form an integrated structure.

Figure 12:
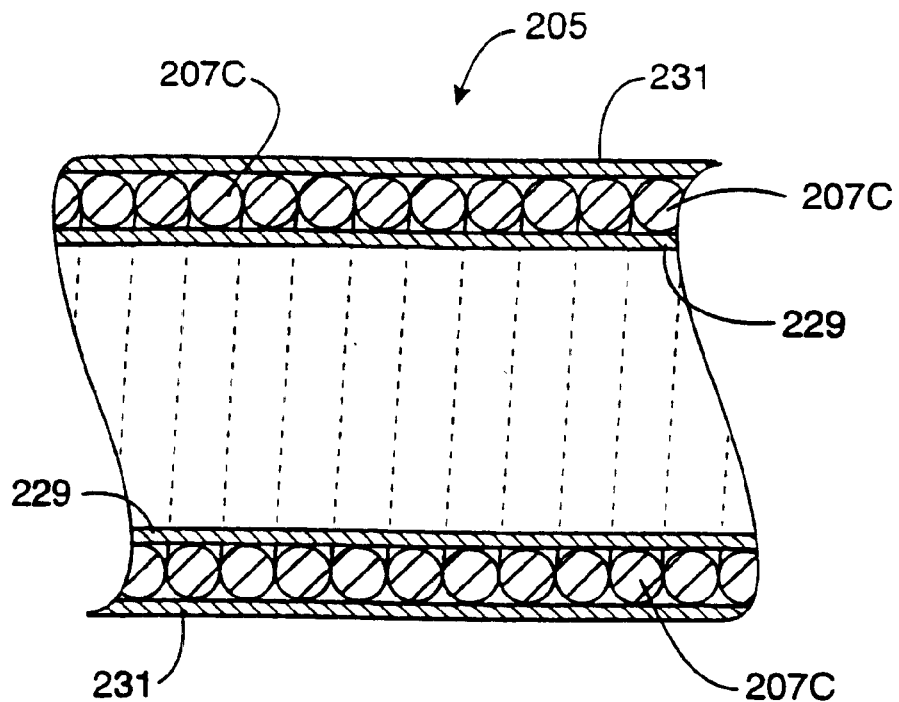
FIG. 12 is a cross-sectional view of a fifth construction for the reinforced section.

Referring to FIG. 12, a fifth preferred construction for the reinforced section 205 is shown. The fifth preferred construction differs from the first through fourth preferred constructions in that the elongate member 207C is not coated before being wrapped around the mandrel. As discussed above, a known method of manufacturing reinforced tubing is to extrude a tube, mount the tube on a mandrel, wind a metal coil around the tube and position another tube over the coil. The tubes and coil are then heated so that the inner and outer tubes bond together. A problem with the known method is that relatively thick walled tubes are formed since the layers must be relatively thick to ensure sufficient strength since the wire must be spaced apart.

The elongate member 207C of FIG. 12 is made of a polymer, preferably 75D polyurethane, so that radially inner and outer polymer layers 229, 231 can fuse to the elongate member 207C to form an integrated structure. Thus, the polymer layers 229, 231 do not need to fuse together completely to form an integrated structure which overcomes a problem with prior art methods of forming reinforced cannulae. The polymer layers 229, 23 1, preferably 80A polyurethane, are positioned on opposite sides of the polymer elongate member 207C. The polymer layers 229, 231 are preferably softer than the polymer used for making the elongate member 207C. The elongate member 207C preferably has a diameter between 0.005–0.020 inch and more preferably between 0.008 and 0.012 inch. The layers 229, 231 preferably have a thickness of 0.002 to 0.015 inch and more preferably 0.005 to 0.10 inch. The elongate member 207C is preferably wound so that adjacent portions of the elongate member 207C contact one another; however, the polymer elongate member 207C may be wound so that a space exists between adjacent portions of the elongate member 207C. Furthermore, although the elongate member 207C preferably has a circular cross-sectional shape the elongate member 207C may have any other shape. The polymer layers 229, 231 may be applied in any manner including coextrusion, dipping or by simply using preformed tubes.

The polymer layers 229, 231 are preferably heated so that they bond with the elongate member 207C. The polymer layers 229, 231 are preferably positioned on both sides of the elongate member 207C before heating the layers 229, 231, however, the layers 229, 231 may also be applied one at a time. By constructing the reinforced section 205 in this manner, the polymer does not need to flow completely between each part of the elongate member 207C to provide an integrated structure since the layers 229, 231 must simply bond to the elongate member 207C rather than having to bond with the opposing layer 229, 231. FIG. 12 depicts the reinforced section 205 before heating; however, after heating the polymer material from the layer 225A and coating 209 fuse together to form an integrated structure.

Figure 13:
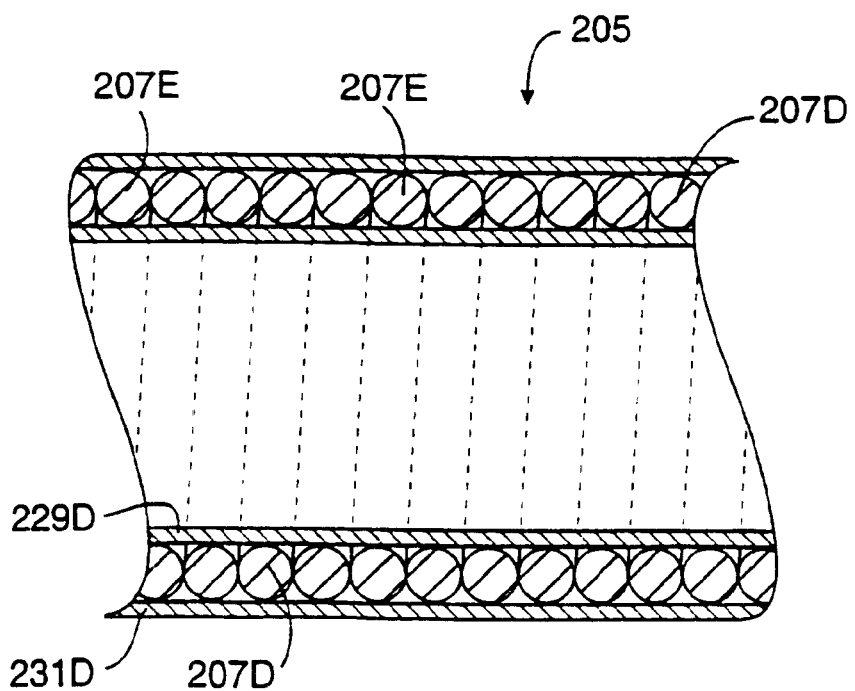
FIG. 13 is a cross-sectional view of a sixth construction for the reinforced section.

Referring to FIG. 13, a sixth preferred construction for the reinforced section 205 is shown with polymer and metal elongate members 207D, 207E wound together. Two polymer layers 229D, 231D are positioned on opposite sides of the elongate members 207D, 207E and may be provided in any manner described above. The polymer layers 229D, 231D are preferably softer than the polymer elongate member 207D. A preferred material for the polymer layers 229D, 231D is 75D polyurethane and a preferred material for the polymer elongate member 207D is 80A polyurethane. The soft polymer layers 229D, 231D are melted to bond to the polymer elongate member 207D thereby forming an integrated structure. The metal elongate member 207E provides structural strength and is preferably a stainless steel wire although any metal may be used. Although it is preferred that the elongate members 207D, 207E have circular cross-sectional shapes, the elongate members may have any other shape. Furthermore, although it is preferred that the elongate members have the same cross-sectional shape, the elongate members may also have different cross-sectional shapes. FIG. 13 depicts the reinforced section 205 before heating; however, after heating the material from the layers 229D, 231D and the elongate member 207D will fuse together to form an integrated structure.

Figure 14:
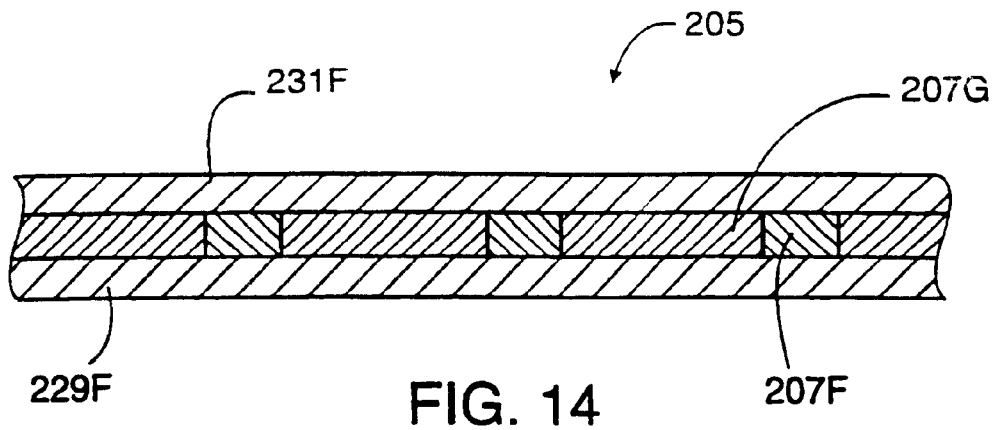
FIG. 14 is a cross-sectional view of a seventh construction for the reinforced section.

Referring to FIG. 14, a seventh preferred construction for the reinforced section 205 is shown. A polymer elongate member 207F is wound together with a flat elongate member 207G. The polymer material for the polymer elongate member 207F may be any polymer and is preferably 75D polyurethane. The flat elongate member 207G is preferably the same as the elongate member 207A described above in connection with FIG. 10. Two layers of polymer 229F, 231F encase the polymer and flat wire elongate members 207F, 207G. The polymer layers 229F, 231F are preferably softer than the polymer material of the elongate member 207F. The polymer layers 229F, 231 F are preferably 80A polyurethane, however, any polymer may be used. The polymer layers 229F, 23 IF may be applied in any manner described above. The polymer layers 229F, 231F preferably have a thickness between 0.002 and 0.010 inch and more preferably between 0.004 and 0.008 inch. The polymer layers 229F, 231F are heated to bond to the polymer elongate member 207. FIG. 13 depicts the reinforced section 205 before heating, however, after heating the layers 229F, 231F and elongate member 207F fuse together to form an integrated structure.

Figure 15:
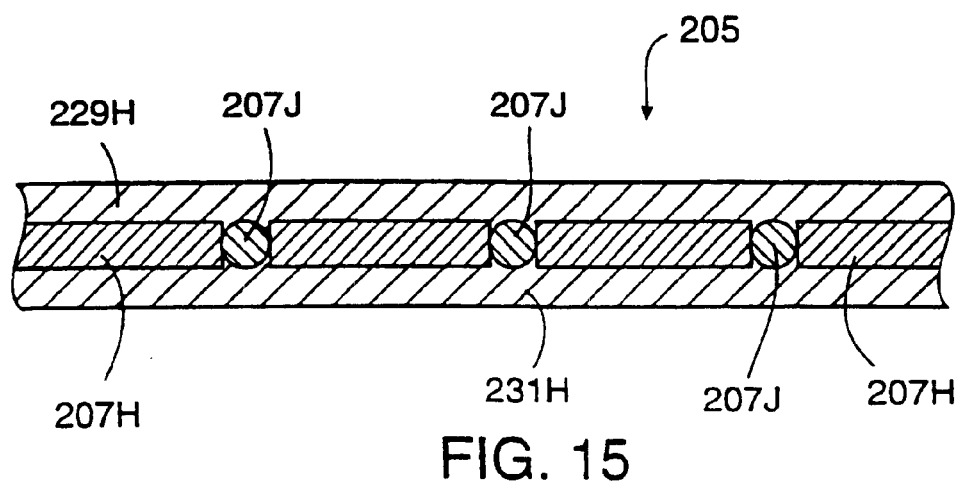
FIG. 15 is a cross-sectional view of a eighth construction for the reinforced section.

Referring to FIG. 15, an eighth preferred construction for the reinforced section 205 is shown. A first elongate member 207H is preferably the same as the elongate member 207A described above in connection with FIG. 10. A second elongate member 207J is made of a polymer and has a thickness between 0.003 and 0.008 inch and more preferably 0.005 inch. Two polymer layers 229H, 231H encase the elongate members. The layers 229H, 231 H are preferably 80A polyurethane having a thickness between 0.002 and 0.010 inch and more preferably between 0.004 and 0.008 inch. The polymer layers 229H, 231 H may be applied in any manner described above. The polymer layers 229H, 231 H are heated to bond to the second elongate member 207J.

Figure 16:
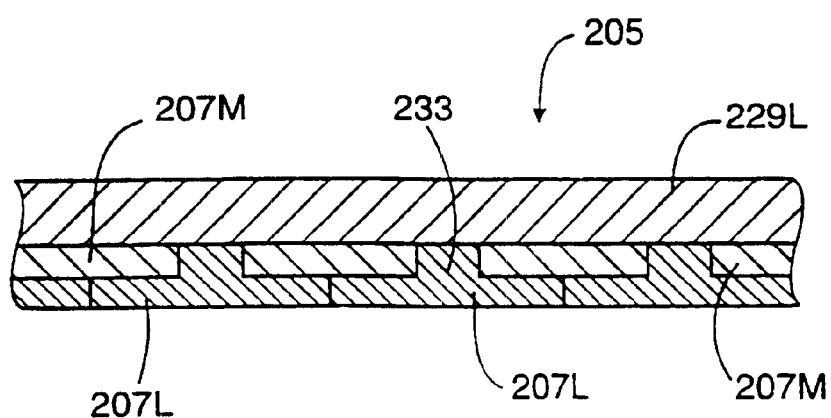
FIG. 16 is a cross-sectional view of a ninth construction for the reinforced section.

Referring to FIG. 16, a ninth preferred construction for the reinforced section 205 is shown. A first elongate member 207L is wound around a mandrel 213 (not shown). The first elongate member 207L is preferably made of polymer, preferably 80A polyurethane, and has a T-shaped cross-sectional shape. The T-shaped cross-sectional shape has a width of 0.028 inch and a height of 0.008 inch. The first elongate member 207L has a radial extension 233 having a width of 0.008 inch. A second elongate member 207M, which is preferably the same as the elongate member 207A described above in connection with FIG. 10, is wound over the first elongate member 207L. A polymer layer 229L is then positioned over the first and second elongate members 207L, 207M and is preferably 80A polyurethane having a thickness of 0.008 inch. The polymer layer 229L may be applied in any manner described above. The polymer layer 229L is then heated so that the polymer layer 229L and the radial extension 233 bond to one another to form an integrated structure.

Figure 17:
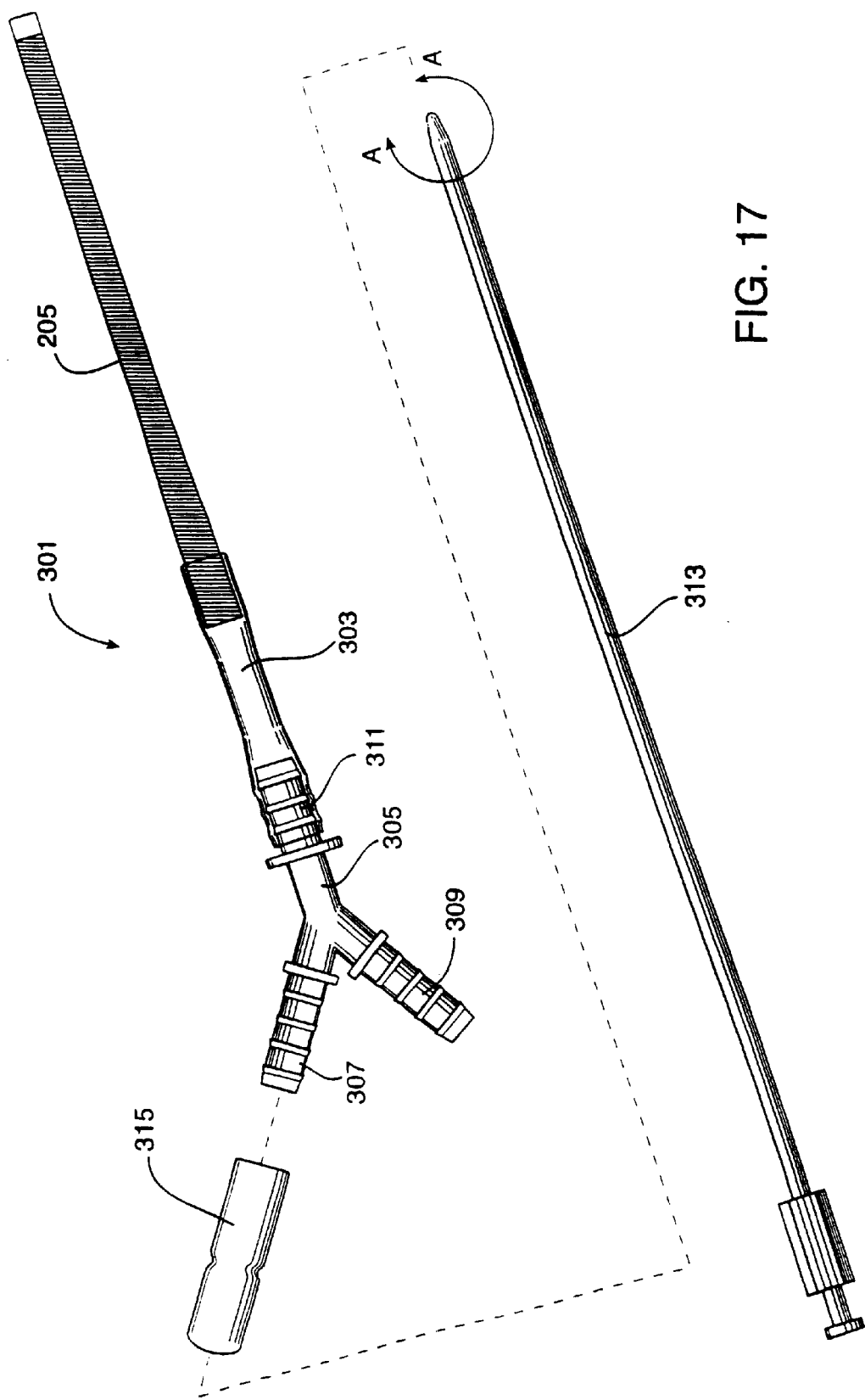
FIG. 17 shows an exploded view of another arterial return cannula.

Referring to FIG. 17, another preferred cannula 301 is shown. The cannula 301 is preferably used as the arterial return cannula for the CPB system described above. The cannula 301 includes the reinforced section 205 as described above. A tube 303 connects the reinforced section 205 to a Y-connector 305 which has first, second and third connections 307, 309, 311. The tube 303 is preferably a flexible tube made of estane 58810 42D polyether polyurethane. When using the cannula 301 for the CPB system described above, the first connection 307 is coupled to a source of oxygenated blood (not shown) while the second connection 309 receives an aortic occlusion catheter (not shown). The aortic occlusion catheter is used to occlude the ascending aorta and deliver cardioplegic fluid for arresting the patient's heart. The second connection 309 preferably receives the extension tube 62 and hemostasis valve 876 for receiving the aortic occlusion catheter in the manner described above in connection with FIGS. 1–4.

Figure 20:
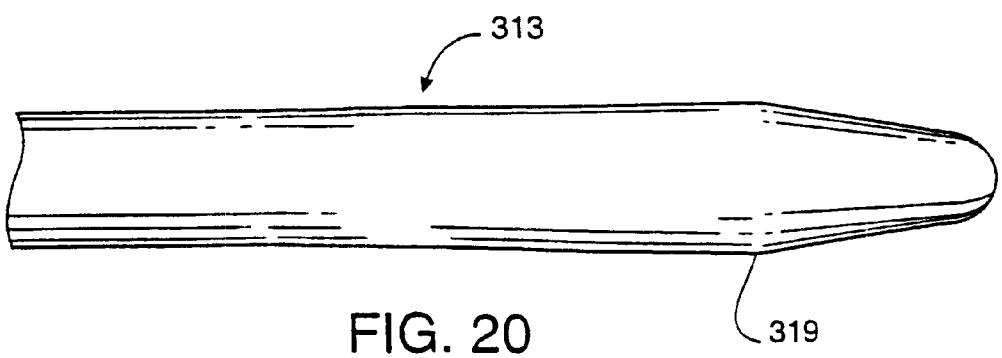
FIG. 20 shows an enlarged view of the distal end of an obturator used with the arterial return cannula of FIG. 17 along line A—A.

A dilator 313 is used to facilitate introduction of the cannula 301 into the patient's artery. A dilator seal 315 seals the space between the cannula 301 and dilator 313. The dilator seal 315 and dilator 313 are removed after the cannula 301 has been introduced into the patient. Referring to FIG. 20, the dilator 313 has an enlarged end 319 which engages an interior wall of the reinforced section 205 when passing through the cannula 301. The enlarged end 319 is preferred so that the dilator 313 does not contact the cannula 301 throughout the length of the dilator 313 thereby reducing the resistance to moving the dilator 313 through the cannula 301.

Figure 18:
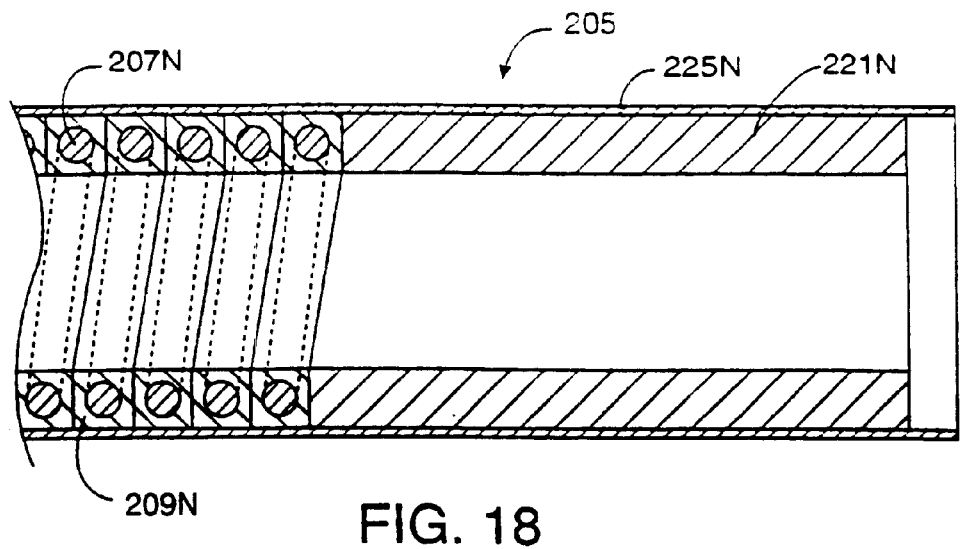
FIG. 18 shows the distal end of the arterial return cannula of FIG. 17 before heating.

Referring to FIG. 18, the method of forming the reinforced section 205 is shown. The reinforced section 205 has an elongate member 207N coated with a coating 209N with the elongate member 207N and coating 209N being any of the members 207A–M and coatings 209A-M described above in connection with FIGS. 6–16. A preferred elongate member 207N is a 0.008 inch stainless steel wire which is coated with 80A durometer polyurethane to a 0.014×0.014 inch cross-section. The elongate member 207N is wrapped around a mandrel (not shown), as described above in connection with FIGS. 6–16, and a soft tip 221 N is butted against the elongate member 207N. The soft tip 221N preferably has the same thickness as the coated elongate member 207N with a preferred material being 90A polyurethane.

A layer 225N, which may be the layer 225 described above, is positioned over the coated elongate member 207N and the soft tip 221 N. The layer 225N is preferably a tube having a thickness of 0.001–0.005 inch, more preferably about 0.003 inch, and is preferably made of the same material as the soft tip 221N. Although it is preferred to provide the layer 225N over the coated elongate member 207N it is understood that the layer 225N may also be positioned on the radially inner surface of the coated elongate member 207N (or not used at all). When the layer 225N is a tube, the tube has an inner diameter which is slightly smaller than the smallest outer diameter of the reinforced section 205. The tube is positioned over the reinforced section by inflating the tube, inserting the coated elongate member 207N into the tube, and deflating the tube so that the tube contracts around the helically wound coated elongated member 207N. By sizing the layer 225N somewhat smaller than the helically wound elongate member 207N, close contact between the layer 225N and elongate member 207N is ensured.

Figure 19:
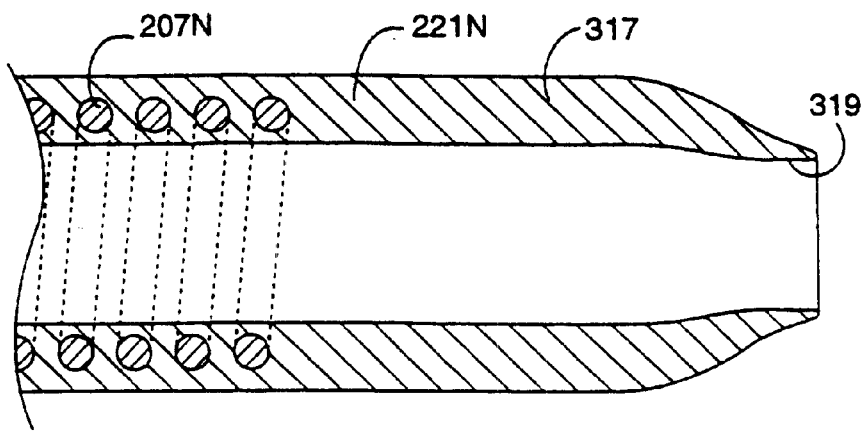
FIG. 19 shows the distal end of the arterial return cannula of FIG. 18 after heating.

A heat shrink tube (not shown) is then positioned over the layer 225N, coated elongate member 207N, and soft tip 221 N. The layer 225N, coated elongate member 207N and soft tip 221N are then heated to fuse the material together to form an integral structure as shown in FIG. 19. The tip of the reinforced member 205 is then trimmed and a tapered mandrel is inserted into the coated elongate member 207N and a heat shrink tube is recovered over the tip to form a bevel 317 at an end 319 of the soft tip 221N which facilitates atraumatic insertion of the cannula 301. The end 319 is curved inward slightly to form a seal with the dilator 313.

The resulting reinforced section 205 preferably has an internal diameter of at least 0.180 inch, more preferably at least 0.200 inch, more preferably at least 0.236, and most preferably at least 0.242 but no more than 0.375 inch. The reinforced section 205 also preferably has a thickness of no more than 0.0020 inch, more preferably no more than 0.018 inch, and most preferably no more than 0.016 inch. When the coated elongate member 207N has a 0.014×0.014 inch exterior surface and the layer 225N has a 0.003 inch thickness, the resulting thickness is about 0.0016 inch since about 0.001 inch is lost when the coated elongate member 207N and layer 225N are compressed with the shrink tube during heating. The unique combination of inner diameter and wall thickness provides a superior cannula as compared to cannulae having conventional constructions.

Figure 21:
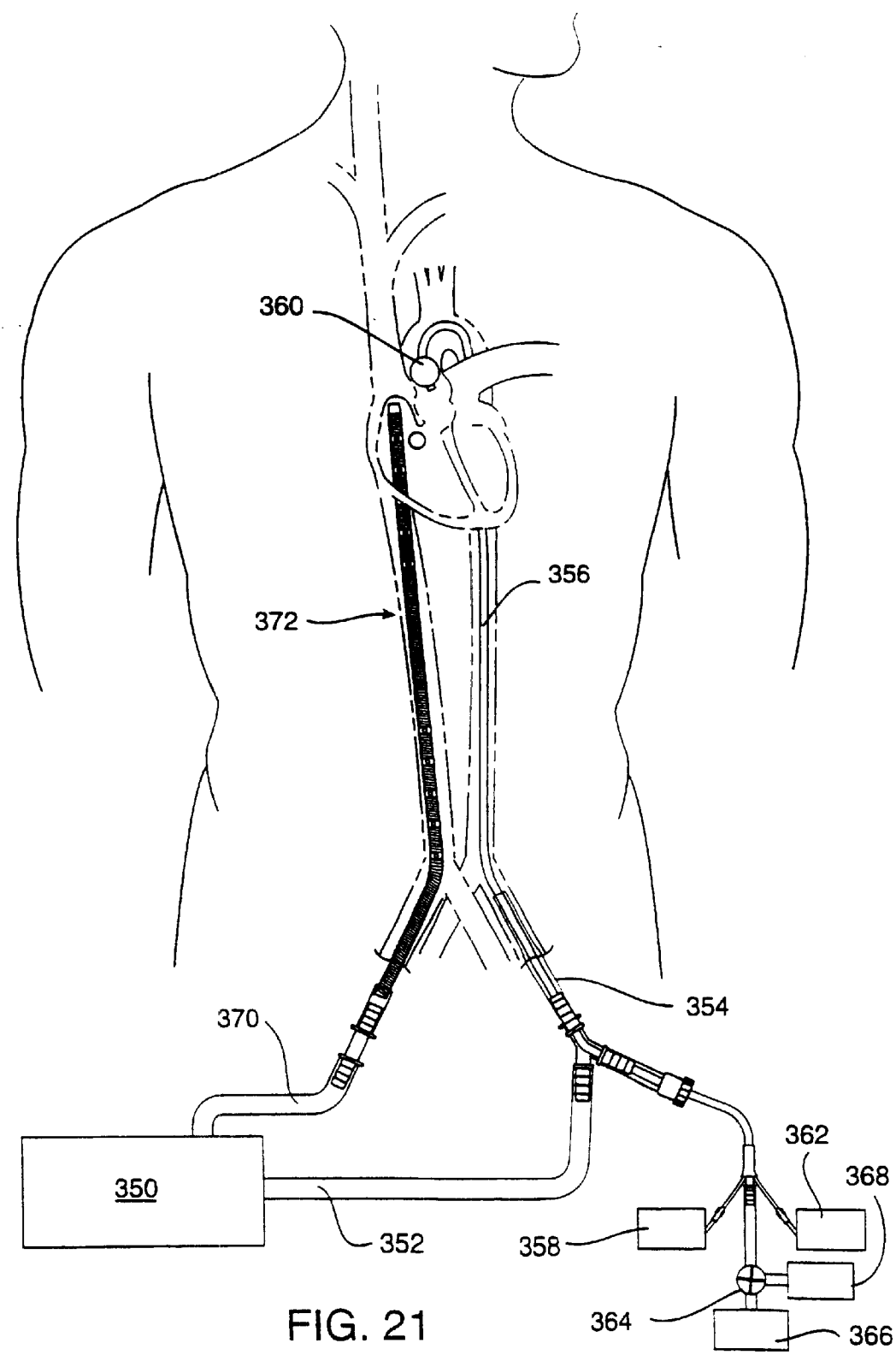
FIG. 21 is a schematic illustration of a cannula constructed according to an alternative embodiment of the invention, wherein the cannula is positioned to withdraw blood from a patient's vascular system.

Referring to FIGS. 21–35, additional embodiments of cannulae constructed according to further aspects of the invention will be described. FIG. 21 illustrates one possible application for such a cannula and schematically depicts a patient on cardiopulmonary bypass in preparation for a minimally invasive cardiac procedure. A CPB system 350 passes oxygenated blood through tubing 352 to an arterial return cannula 354 which is positioned in the patient's arterial system. An aortic occlusion catheter 356 passes through the arterial cannula 354 and is used to block blood flow through the ascending aorta and deliver cardioplegic fluid to arrest the heart for performing surgery on the heart and great vessels. The aortic occlusion catheter 356 is inserted through the same lumen in the arterial cannula 354 which is used to return arterial blood to the patient, and thus arterial blood essentially passes in the annular space between the aortic occlusion catheter and the arterial return cannula. The arterial return cannula 354 is coupled to a pump 358 for inflating a balloon 360 which occludes the aorta, a pressure sensor 362, and a valve 364 which controls communication of the arterial cannula 354 with a source of cardioplegic fluid 366 and a source of vacuum 368.

The CPB system 350 withdraws venous blood through tubing 370 which communicates with a venous return cannula 372 positioned in the patient's venous system. The cannula 372 is constructed according to an additional aspect of the invention and, in the embodiment illustrated in FIG. 21, is positioned in the patient's femoral vein, although other veins such as the jugular or subclavian vein could be used. In the illustrated and preferred embodiment, the venous cannula 372 has reinforced sections and nonreinforced sections.

Figure 22:
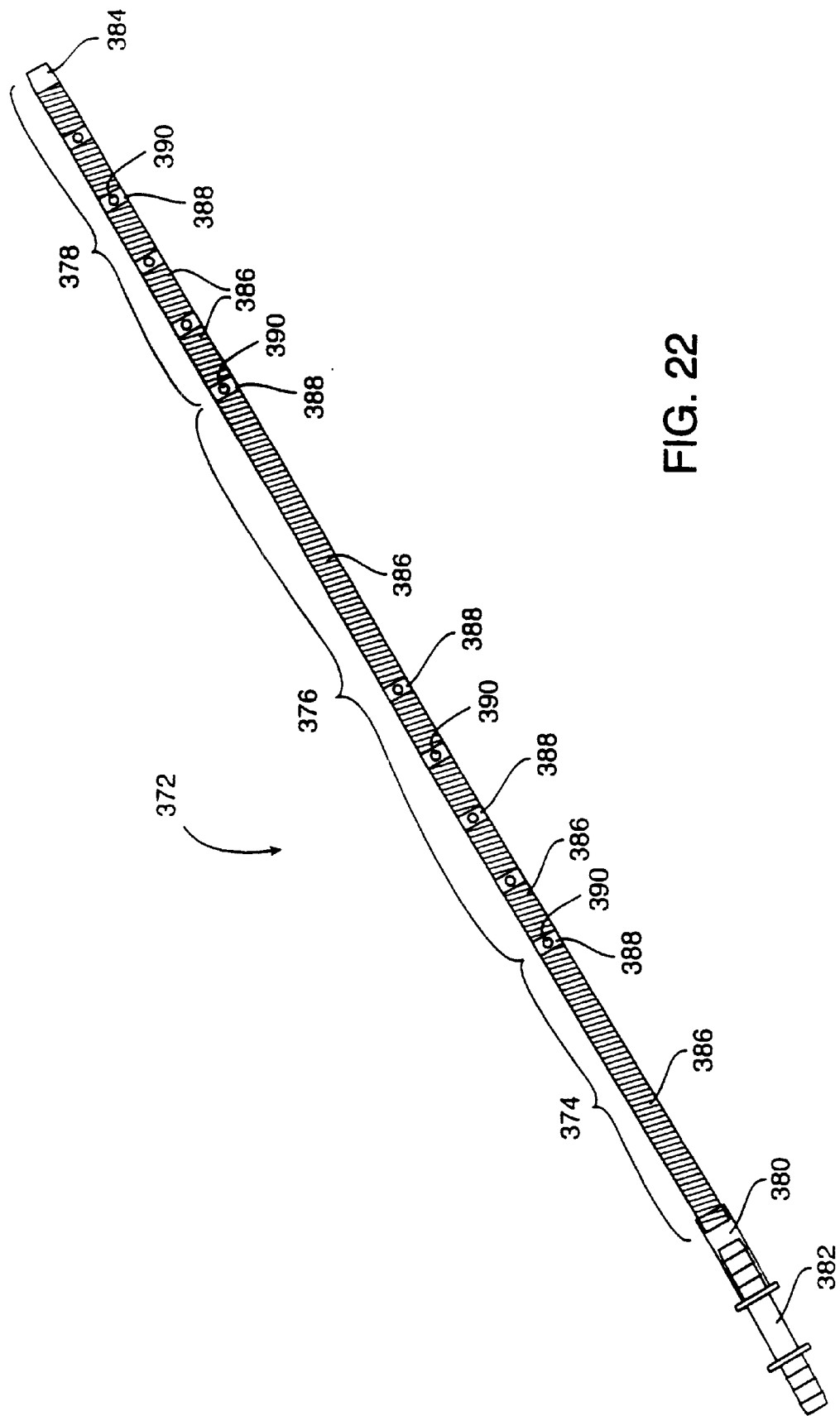
FIG. 22 is an elevation view of the cannula shown in FIG. 21.

More particularly, as shown best in FIG. 22, the cannula 372 comprises a tubular body which, for explanatory purposes, is shown as including a proximal portion 374, a central portion 376 and a distal portion 378. A lumen extends through the cannula 372. A connector element in the form of a sleeve 380 is provided on the proximal end of the cannula 372 and is used to attach the cannula to a connector 382 which is connected to the tubing 370 (FIG. 21). The distal end of the cannula 372 has an atraumatic tip 384 for minimizing the risk of damaging the vessel tissue upon inserting the cannula into a patient's vascular system.

The cannula 372 is constructed so as to include reinforced sections 386 each of which, in the preferred embodiment, comprises an elongate member encased in a material as described above with respect to the previous embodiments. The reinforced sections of the cannula, however, may take other forms, for example, tubing wrapped with a reinforcing member. In addition to the sections 386, the cannula 372 includes nonreinforced sections 388 which are substantially free of the elongate reinforcing member. In the preferred embodiment, the sections 388 are completely free of the reinforcing member and comprise plain tubing sections. The sections 388 are provided with one or more openings 390 for withdraw fluid from (or delivering fluid to) the patient's vascular system. The openings 390 pass radially through the wall of the tubing sections 388 to communicate with the lumen of the cannula 372.

In the preferred embodiment illustrated in FIG. 22, the proximal portion 374 of the cannula 372 comprises over its length an elongated reinforced tubing section 386. The proximal portion 374 thus is defined as the portion of the cannula 372 extending between the proximal end of the cannula and the most proximal section 388 with an opening 390. The central portion 376 of the cannula 372 comprises over part of its length reinforced sections 386 alternately disposed with tubing sections 388, and over the remaining part of its length an elongated reinforced section 386. The distal portion 378 of the cannula 372 comprises over its length reinforced sections 386 alternately disposed with tubing sections 388. As such, there are openings 390 in the tubular sections 388 in the central and distal portions 376, 378, and thus fluid will enter (or exit) the lumen of the cannula 372 through the central and distal portions, as well as through the distal opening at the tip 384.

When using the cannula 372 as a venous withdrawal cannula configured to be positioned in the femoral artery, as shown in FIG. 21, the location of the nonreinforced sections 388 with respect to the overall length of the cannula is such that the openings 390 are disposed adjacent to veins that carry a considerable amount of blood (e.g., up to two-thirds of the blood carried by the patient's venous system). In particular, as shown in FIG. 21, the nonreinforced sections 388 of the central portion 376 of the cannula 372 are located superior to the bifurcation of the inferior vena cava so that blood passing from the renal and/or hepatic veins drains into the openings 390 in these sections 388. In addition, blood passing from arteries in the legs also drains into these openings 390. As a result, a significant amount of blood does not have to travel to the inferior or superior vena cava (or the right atrium) in order to be drained through the cannula 372. This permits lower pump pressures to be used as compared to conventional venous cannulae.

Accordingly, in the exemplary application illustrated in FIG. 21, blood passes into the openings 390 in the tubular sections 388 located at the central and distal portions 376, 378 of the cannula 372. and is fed to the CPB system 350. Depending on the particular procedure being performed, the patient's physiology, anatomy, etc., the size and location of the nonreinforced tubular sections 388 and the openings 390 may be altered to achieve desired fluid pressures and/or flow rates.

As an example, in the venous cannula embodiment shown in FIG. 21, the total working length of the cannula 372 (i.e., the portion of the cannula extending from the sleeve 380 to the distal tip 384 which is able to be inserted into the patient's vein or artery) is preferably within a range of from about 50 to 75 cm, the outside diameter is preferably within a range of from about 19 to 32 French, and more preferably about 21 to 25 French. The inside diameter of the cannula is preferably within a range of from about 16 to 29 French, and more preferably about 18 to 22 French.

In addition, for a venous cannula having a length within this range, the most proximal opening 390 (i.e., the opening which is located in the patient's vascular system during use and is nearest the proximal end of the cannula) is preferably located at least about 25 cm from the distal end of the cannula, and more preferably at least 30 cm. However, for some applications it may be desirable to have the most proximal opening located at least 40, 50 or 60 cm from the distal end of the cannula. The length of the proximal portion 374 (between the proximal end of the cannula and the most proximal opening) is preferably within a range of from about 5 to 15 cm.

Further, the length of each reinforced tubular section 386 is preferably within a range of from about 2 to 50 mm, and more preferably about 10 to 25 mm, while the length of each tubular section 388 is preferably within a range from about 3 to 20 mm, and more preferably about 5 to 12 mm. The openings 390 preferably have a diameter within a range of from about 0.020 to 0.250 inch, and more preferably about 0.080 to 0.120 inch.

When used to withdraw blood from a patient's vascular system, this cannula configuration is preferably used to achieve flow rates within a range of from about 0.1 to about 7.5 liters/minute, and more preferably from about 1 to about 6 liters/minute, at fluid pressure differentials preferably within a range of from about 0 to 250 mm Hg, and more preferably about 0 to 100 mm Hg.

As mentioned above, the venous cannula could be constructed for use in veins other than the femoral, for example, the jugular or subclavian vein. As an example, for a cannula for use in the jugular or subclavian vein, the total length of the cannula is preferably within a range of from about 10 to 20 cm, the outside diameter is within a range of from about 8 to 17 French, and more preferably about 12 to 16 French, while the inside diameter is within a range of from about 5 to 14 French, and more preferably about 9–13 French. The distance from the most proximal opening 390 (i.e., the opening which is located in the subclavian or jugular vein during use and is nearest the proximal end of the cannula) to the distal end of the cannula is preferably at least about 5 mm, more preferably at least 4 cm, even more preferably 8 cm, and most preferably 12 cm.

Figure 23:
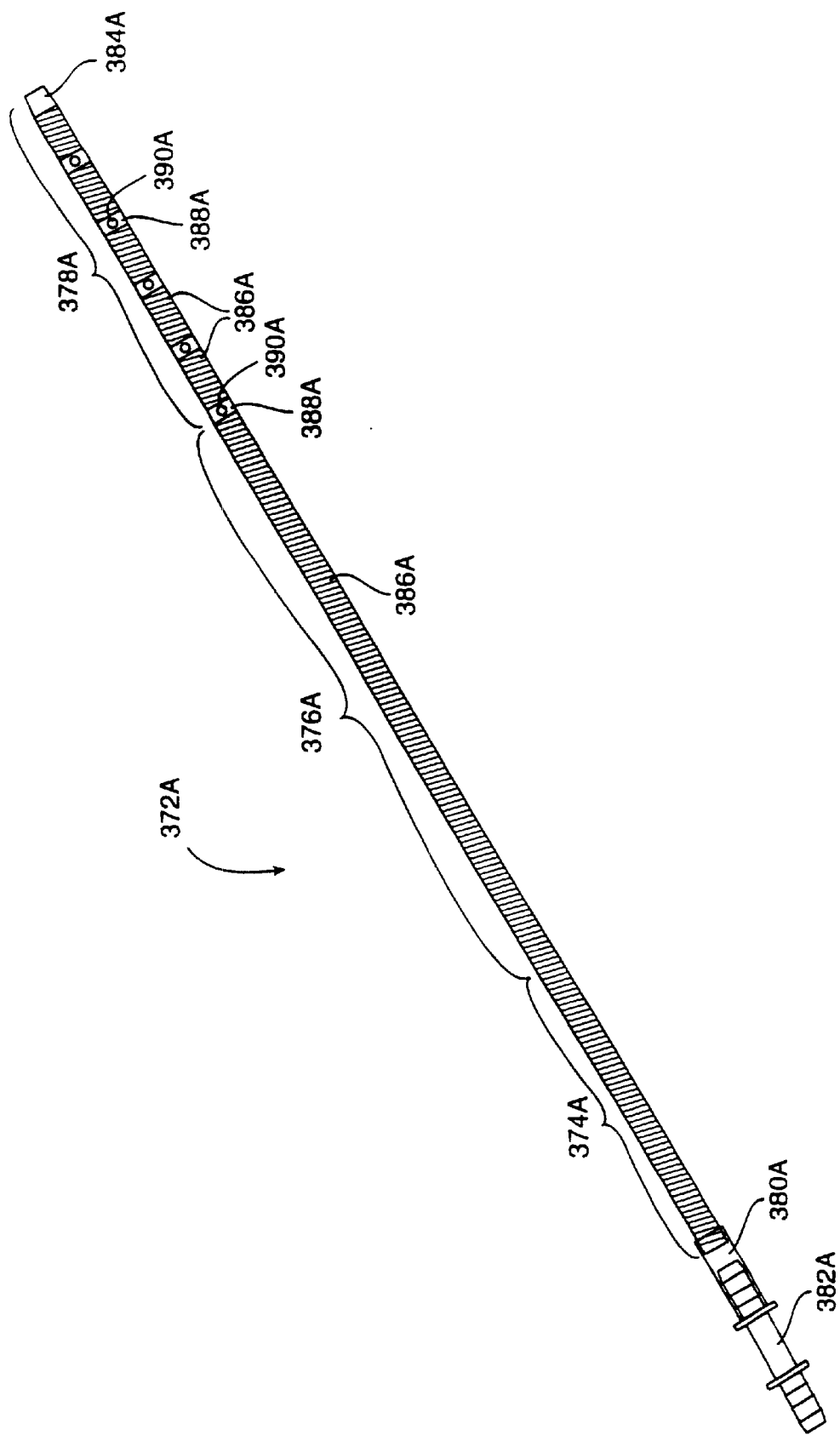
FIGS. 23 and 24 are elevation views of cannulae constructed according to additional embodiments of the invention.
Figure 24:
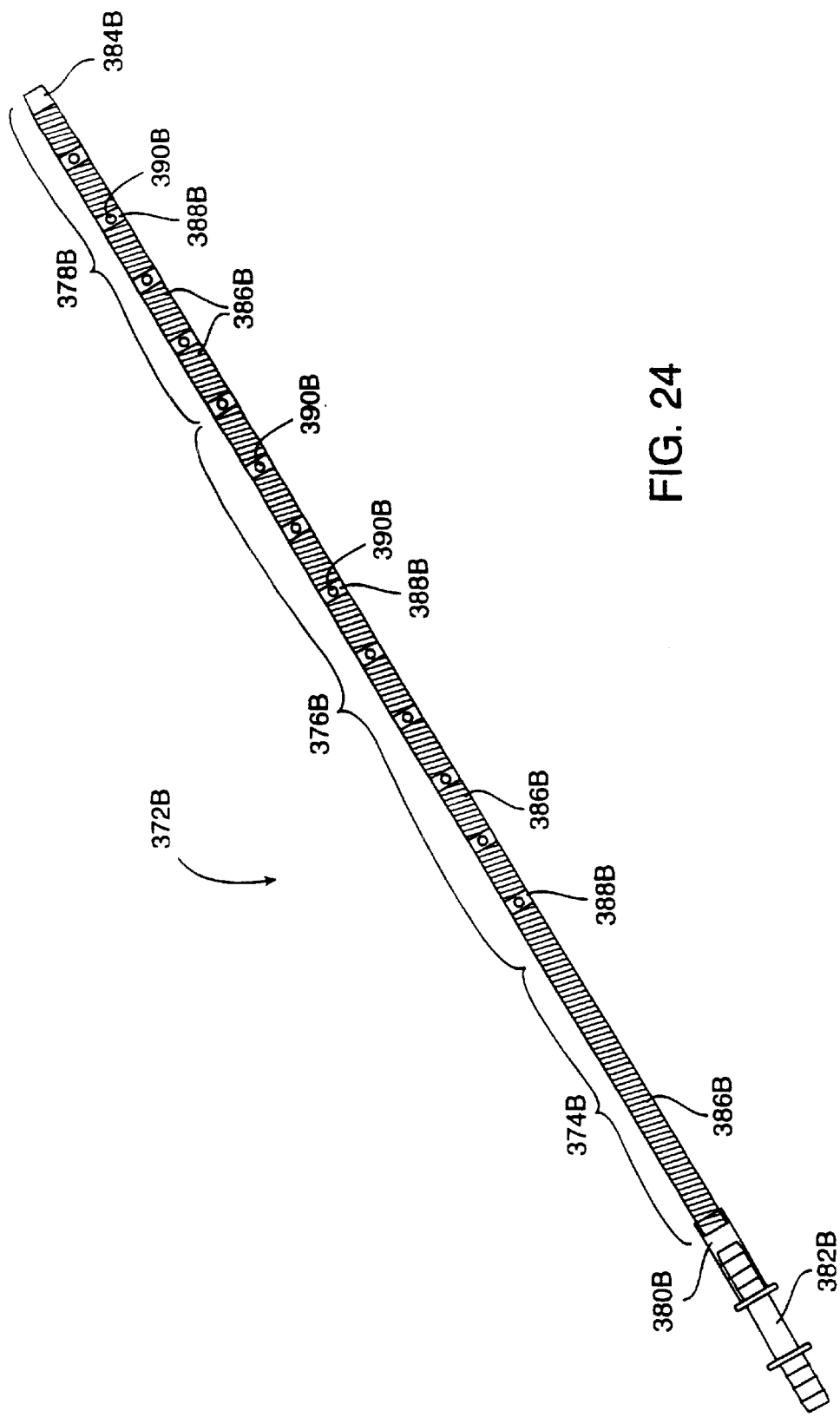

It will be recognized, or course, that alternative cannulae configurations may be used, several examples of which are illustrated in FIGS. 23 and 24. In FIG. 23, the cannula 372A includes a proximal portion 374A and a central portion 376A each of which comprises over their length an elongated reinforced tubing section 386A. A distal portion 378A comprises over its length reinforced sections 386A alternately disposed with tubing sections 388A having openings 390A. Thus, fluid will pass into (or out of) the openings 390A in the tubing sections 388A of the distal portion 378A.

In FIG. 24, the cannula 372B includes a proximal portion 374B which comprises over its length a reinforced section 386B. A central portion 376B and distal portion 378B each comprise over their length reinforced tubing sections 386B alternately disposed with tubing sections 388B having openings 390B. Therefore, fluid will pass into (or out of) the openings 390B in the tubing sections 388B of the central and distal portions 376B, 378B. Persons skilled in the art will appreciate that many configurations other than those illustrated may be utilized for various applications. For example, the proximal portion of the cannula may comprise over its length alternating reinforced and nonreinforced sections, the distal portion may comprise over its length an elongated reinforced portion, etc. Further, while the cannulae 372, 372A and 372B are described in connection with their preferred use as venous withdrawal cannulae, it should be recognized that they are equally usable (as disclosed or modified) in other applications including arterial return cannulae.

Figure 25:
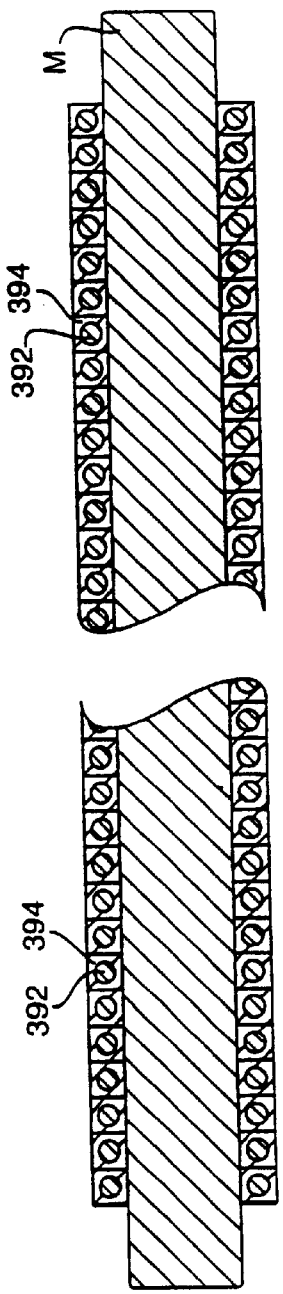
FIGS. 25–33 are elevation views illustrating the steps of a preferred method of manufacturing the cannula shown in FIGS. 21 and 22.
Figure 26:
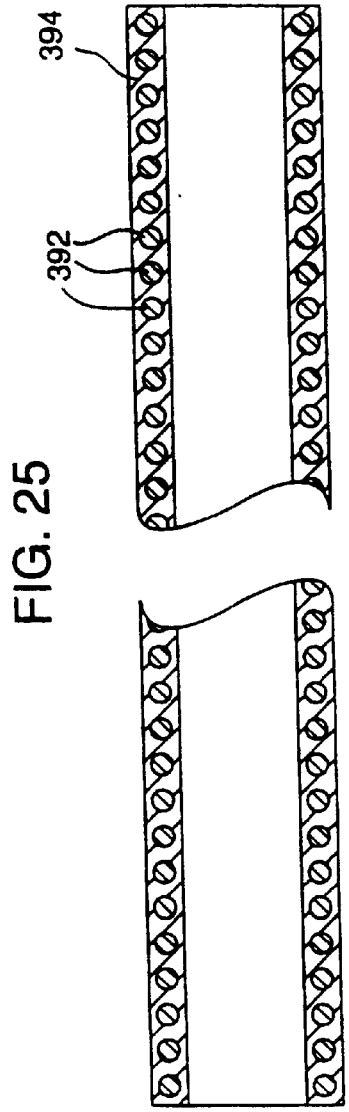

Referring to FIGS. 25–33, a preferred method of manufacturing the cannula 372 will be described. The steps shown in FIGS. 25 and 26 are carried out form a reinforced tubular body comprising an elongate member encased in material. The reinforced tubular body is preferably formed according to any of the methods described above with respect to the previous embodiments; however, the reinforced body could be formed by conventional methods of producing reinforced tubular structures. Thus, in the preferred embodiment, an elongate member 392 coated in a material 394 is wrapped around a teflon coated mandrel M, preferably in a helical manner such that the opposing sides of each coil contact each other. A polyester insulated heat shrink wrap is placed over the coated elongate member 392 and the assembly is heated to bond the adjacent turns to form a reinforced tubular body, as shown in FIG. 26.

The materials used for the elongate member 392 and coating 394 are preferably as described above with respect to the previous embodiments. The size of the elongate member 392 and the coating layer 394, as well as any additional coating layer (if used—not shown in FIG. 26 ) are also preferably as described above.

Figure 27:
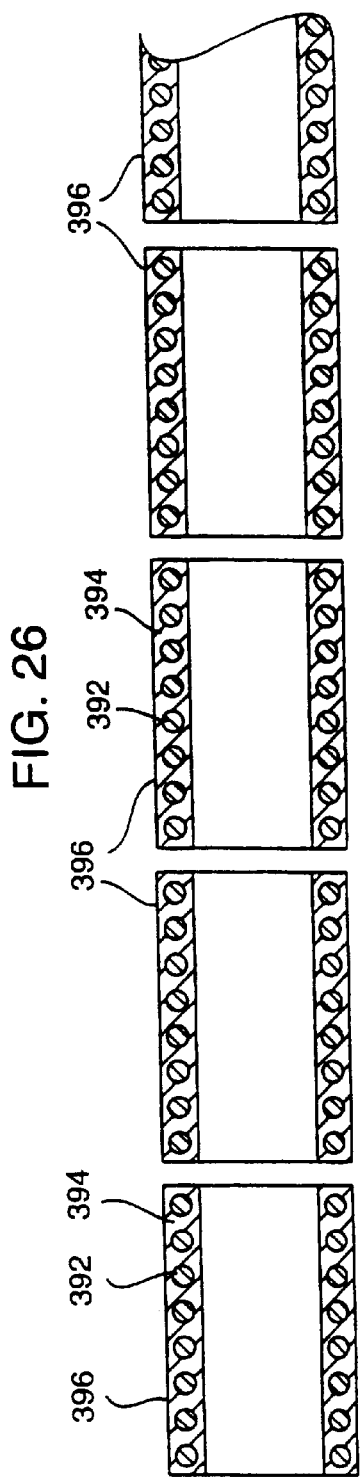

Referring to FIG. 27, the reinforced tubular body of FIG. 26 is separated, for example by being cut, to form individual reinforced tubular sections 396 each of which comprises the elongate reinforcing member 392 encased in the material 394. The number and size of reinforced tubular sections 396 depends on the desired configuration of the cannula. For example, in producing the cannula shown in FIG. 22, a reinforced section having a length corresponding to the proximal portion 374 of the cannula will be cut from the reinforced tubular body shown in FIG. 26. Next, a number of reinforced tubular sections 396 are cut from the reinforced tubular body to provided the reinforced sections 386 which form part of the central and distal portions 376, 378 of the cannula.

Figure 28:
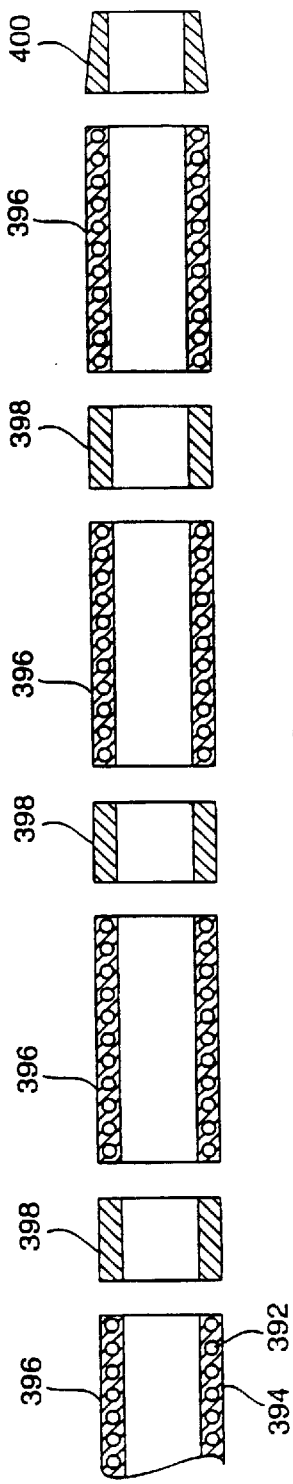

The reinforced tubular sections 396 are positioned next to each other with tubular sections 398 therebetween, as shown in FIG. 28. The tubular sections 398 are preferably plain tubing which is substantially, and more preferably completely free of the elongate reinforcing member 392. The tubular sections 398 are also preferably substantially, and more preferably completely free of any other reinforcing element. The tubular sections 398 may be formed of any suitable material, for example, polyurethane, PEBAX, PVC, KRATON, Silicone, or polycarbonate.

Figure 29:
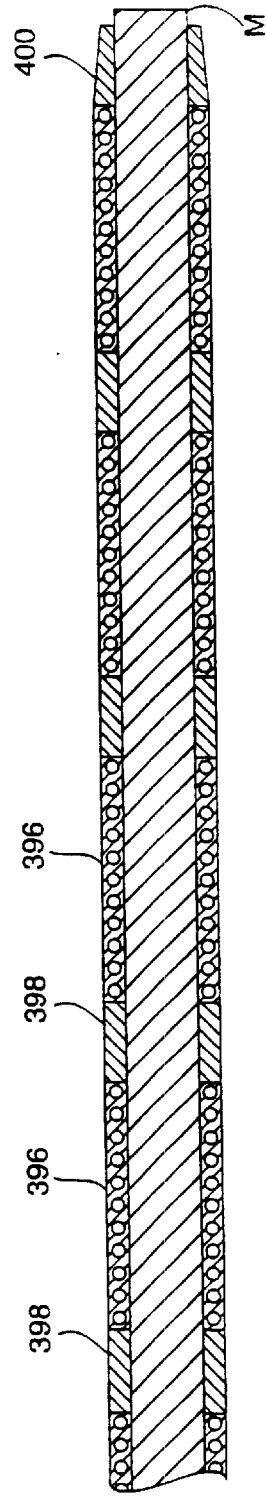

The respective tubular sections 396, 398, disposed as shown in FIG. 28, are positioned over a mandrel M in butt-joint fashion, as shown in FIG. 29. However, prior to placing the sections 396 on the mandrel, it is desirable to rewind or otherwise manipulate the ends of each elongate member 392 (which are exposed at the ends of each tubular section 396) in order to prevent the elongate members from unwinding upon the application of heat. This may be accomplished by rewinding the ends of the reinforcing element over a mandrel having a smaller diameter than the mandrel over which the respective tubular sections are disposed.

Figure 30:
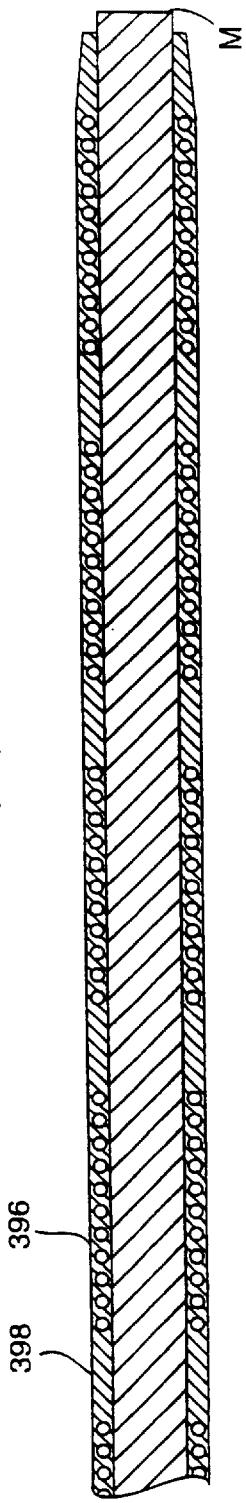

The distal portion 378 of the cannula is illustrated in FIGS. 28–30; thus, a tubular section 400 is positioned next to the last section 396 to form the atraumatic tip 384. After the ends of the reinforcing elements have been rewound as described above, the respective tubular sections 396, 398 are fused together, for example, by heating as described above with respect to the previous embodiments. The resulting cannula is shown (on the mandrel M) in FIG. 30. As can be seen, the respective tubular sections 396, 398 are bonded together to form an integral tubular structure. It should be noted that the remaining portions of the cannula (not shown in FIGS. 28–30) will correspond to the desired cannula construction (for example, as shown in FIGS. 22–24). That is, the tubular sections 398 and the reinforced sections 396 will be disposed alternately according to the construction of each desired portion of the cannula.

Figure 31:
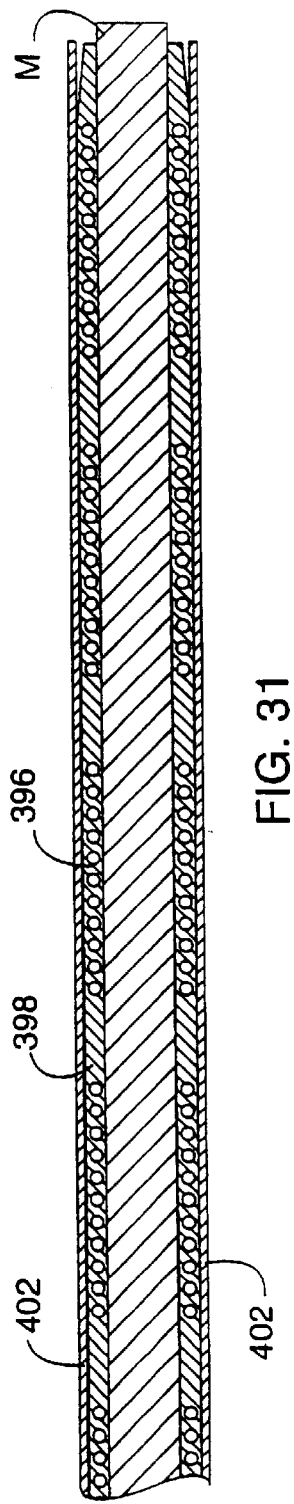
Figure 32:
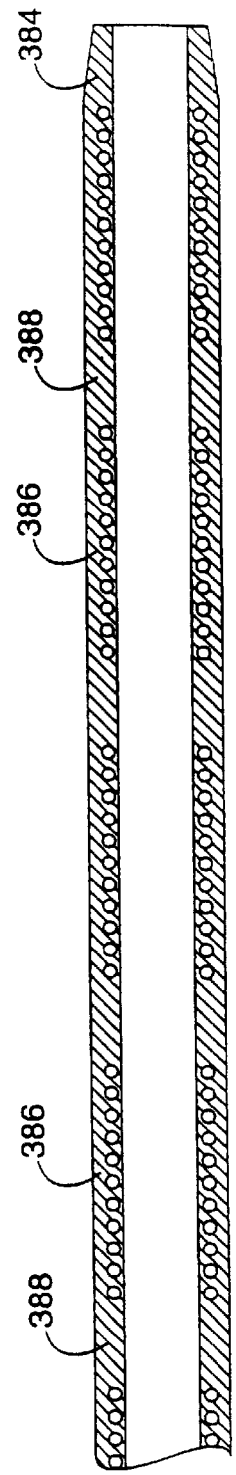
Figure 33:
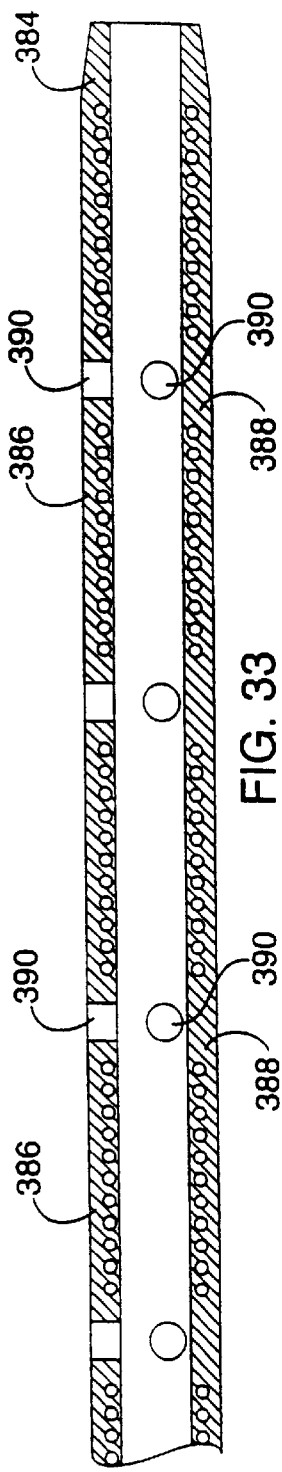

FIG. 31 shows the cannula of FIG. 30 after an additional layer 402 has been disposed over the exterior surface of the cannula. It is preferred to utilize an additional layer to further secure the respective tubular sections 396, 398 together. The layer 402, which may be polyurethane or any other suitable material discussed above with respect to the previous embodiment, is placed over the cannula and the assembly is heated to bond the layer 402 to the cannula, thereby forming an integral structure (FIG. 32) which comprises the reinforced sections 386 and nonreinforced sections 388. Alternatively, the layer 402 could be placed over the tubular body as shown in FIG. 29 and then heat applied to simultaneously bond the respective tubular sections together and the layer 402 to the exterior of the sections.

Next, one or more openings are formed in the sections 388 of the cannula which are substantially free of the elongate reinforcing member 392. In the illustrated embodiment, three circular openings 390 are formed in each tubular section 388 so as to extend radially outward through the wall of the cannula, the openings preferably being evenly spaced about the periphery of the cannula. It will be appreciated, however, that any number, configuration or size openings may be used depending on the fluid flow parameters for a desired application.

Figure 34:
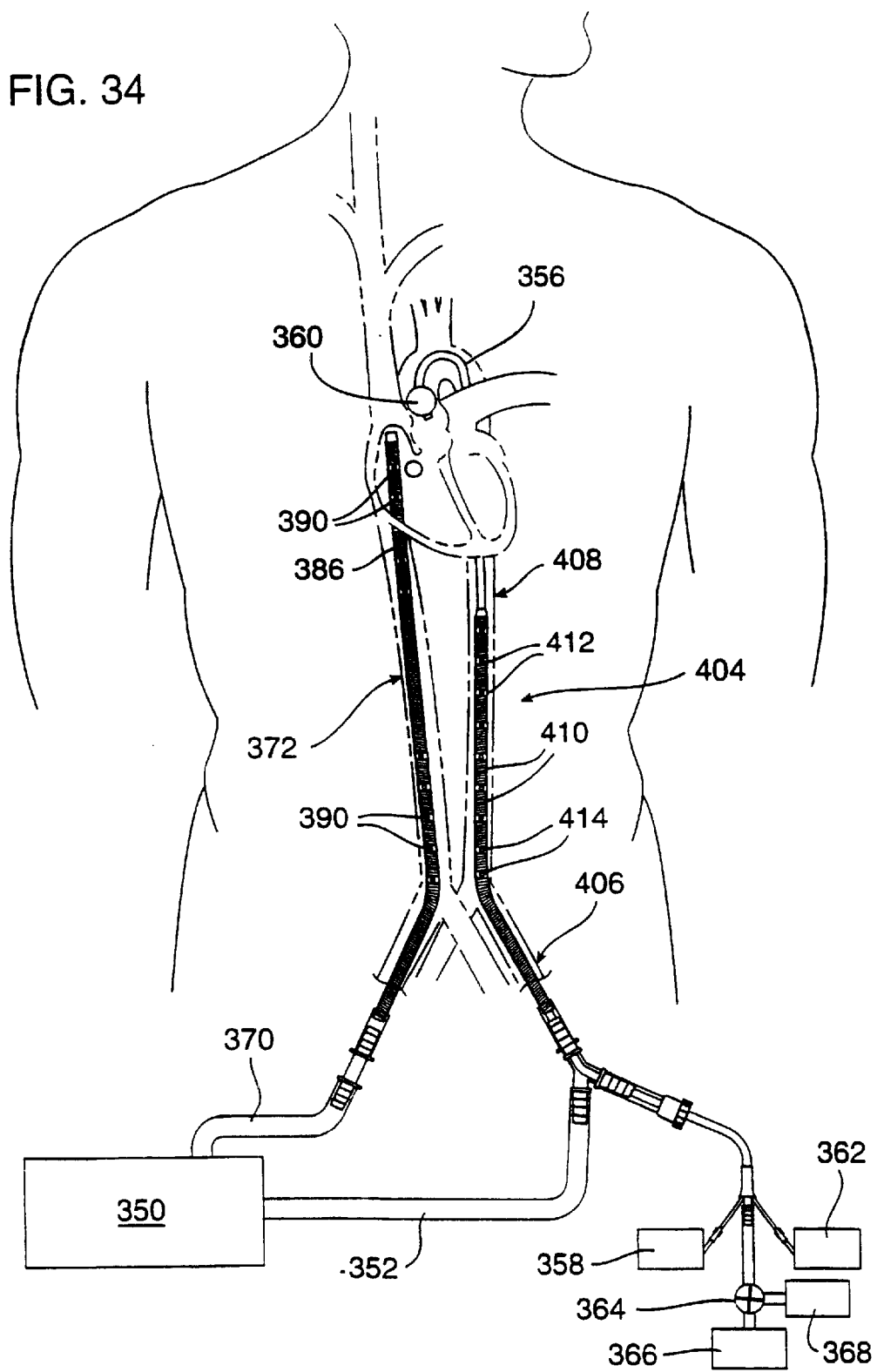
FIG. 34 is a schematic illustration of the cannula shown in FIG. 21 positioned to withdraw blood from a patient's vascular system, along with a second cannula positioned to deliver blood to the patient's vascular system.

FIG. 34 illustrates an alternative application of the invention in which, in addition to the venous withdrawal cannula 372, a cannula 404 is positioned in the patient's femoral artery for use as an arterial return cannula. As shown, the cannula 404 has a similar construction as the cannula 372 in that it includes a proximal portion 406 which is reinforced over its entire length. The remaining portion 408 of the length of cannula 404 comprises alternately disposed reinforced tubular sections 410 and nonreinforced tubular sections 412, the nonreinforced tubular sections 412 having openings 414 for delivering blood to the patient's arterial system. The openings 414 are preferably located superior to the aortic bifurcation in close proximity to the renal and hepatic arteries.

The aortic occlusion device 356 passes through the lumen of the cannula 404 and the balloon 360 occludes the ascending aorta. Blood is oxygenated by the CPB system 350 and passes to the cannula 404 via tubing 352. The oxygenated blood enters the annular space between the wall of the cannula 404 and the aortic occlusion device 356 and exits the openings 390 into the patient's arterial system. It should be recognized that the arterial return cannula 404 may be used with or without the venous return cannula 372, and may have the same or a different construction than the cannula 372.

As an example, in the embodiment of an arterial cannula configured for use in a femoral artery, as shown in FIG. 34, the total length of the cannula 404 is preferably within a range of from about 4 and 40 cm, and more preferably about 6 to 40, the outside diameter is preferably within a range of from about 15 to 32 French, and the inside diameter is preferably within a range of from about 12 to 29 French.

In addition, for an arterial cannula having a length within this range, the most proximal opening 414 (i.e., the opening which is located in the femoral artery during use and is nearest the proximal end of the cannula) is preferably located at least about 5 cm from the distal end of the cannula, more preferably at least 10 cm, and most preferably at least 20 cm from the distal end of the cannula. The length of the proximal portion 406 (between the proximal end of the cannula and the most proximal opening 414) is preferably within a range of from about 5 to 15 cm.

The length of each reinforced tubular section 410 and each nonreinforced section 412, as well as the size of the openings 414, is preferably the same as described above in connection with the embodiment of FIGS. 21 and 22.

An arterial cannula also could be constructed for use in arteries other than the femoral, for example, the subclavian artery. A preferred cannula for such an application would be constructed the same as the venous cannula described above for use in the jugular or subclavian vein.

Figure 35:
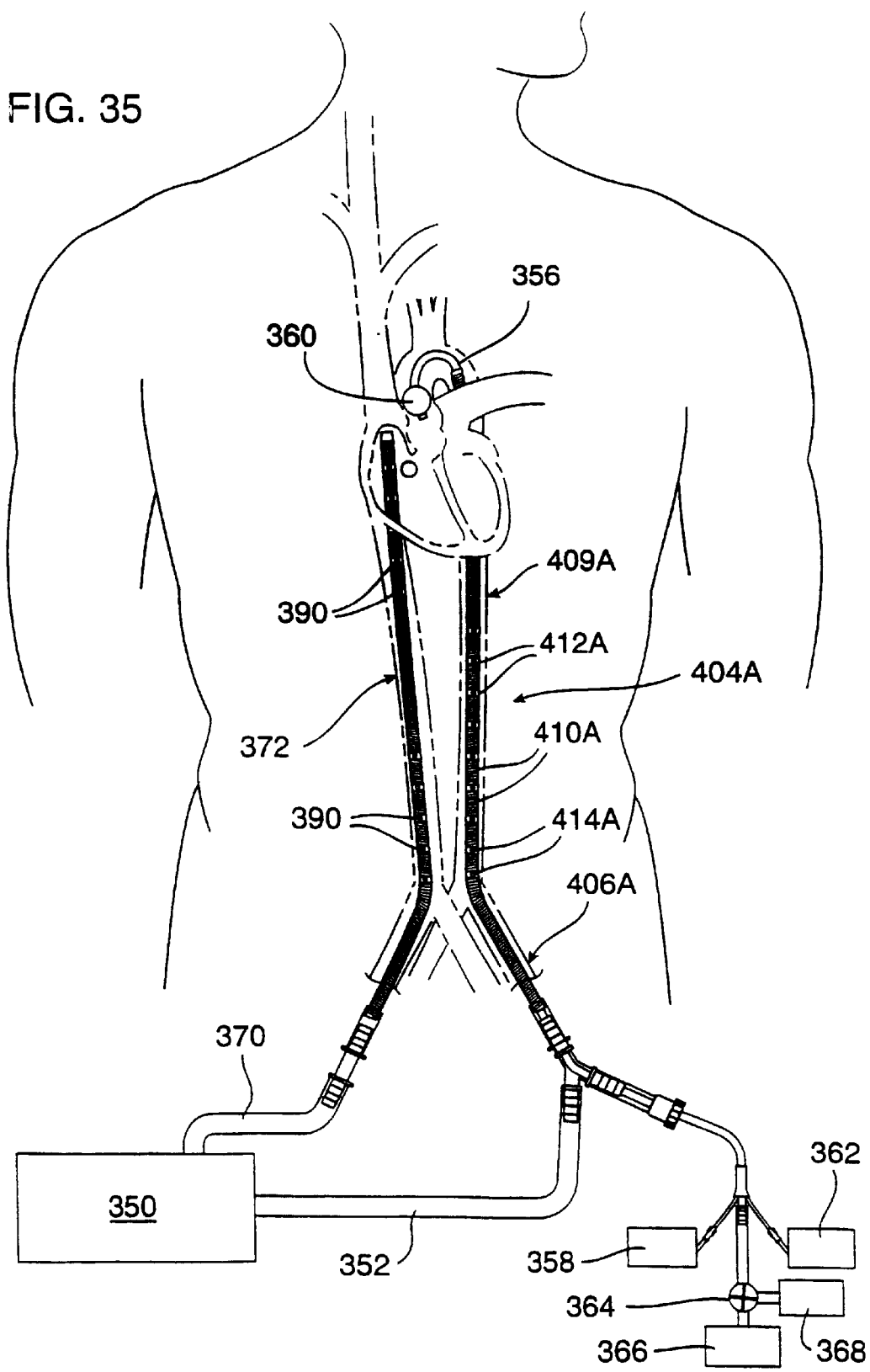
FIG. 35 is a schematic illustration of the cannula shown in FIG. 21 positioned to withdraw blood from a patient's vascular system, along with a second cannula constructed according to another embodiment of the invention positioned to deliver blood to the patient's vascular system.

FIG. 35 illustrates yet another embodiment of an arterial cannula 404A positioned in the patient's femoral artery for use as an arterial return cannula (along with a venous withdrawal cannula 372). As shown, the cannula 404A has a similar construction as the cannula 404 shown in FIG. 34 except that the cannula 404A has an elongate distal portion 409A that extends from the portion 408A to the aortic arch. The elongate portion 409A is reinforced over its entire length.

Another aspect of the invention which is embodied in the preferred and illustrated embodiments of a cannula, e.g., cannulae 372 and 404, is the provision of one or more proximal openings located in a proximal section of the tubular body forming the cannula, i.e., the proximal section being defined as the section of the cannula located between the proximal end and midpoint of the tubular body. The openings are provided in the proximal section of the cannula so that they are located adjacent to veins or arteries that carry a significant amount of the blood in a patient's circulatory system. In the preferred embodiments, the distal section of the cannula (between the midpoint and distal end of the tubular body) also is provided with openings that pass through the wall of the cannula and, along with the open distal end, allow blood to enter or exit the cannula.

However, according to this aspect of the invention, the proximal section of the cannula is preferably provided with a sufficient number and/or size of openings so that the area defined by the openings in the proximal section account for at least 25 to 40%, more preferably at least 50%, and most preferably at least 60% of the total flow area through which fluid enters or exits the cannula from or into the patient. In the preferred embodiment, for example, the cannula 372 shown in FIG. 22, the total flow area would equal the area of all of the openings 390, as well as the area of the open distal end 384. Thus, the area of the openings 390 in the central section 376 of the cannula would comprise at least 40% of the area of the openings 390 in the distal portion 378 combined with the area of the open end 384.

The cannula 372 shown in FIG. 22 could also be constructed so that the area of the openings in the proximal portion are at least 50% (or at least 60%) of the total flow area. For example, relative to the configuration shown in FIG. 22, one, two (or more) sections 390 could be added to the proximal portion 374 of the cannula, resulting in a greater percentage of the total flow area being disposed on the proximal section of the cannula. Alternatively, or additionally, fewer sections 388 could be provided in the distal portion 378 of the cannula, which would also result in a greater percentage of the total flow area being disposed on the proximal section of the cannula. It should be appreciated that the number of sections 388 (which include the openings 390) may be varied to achieve the desired distribution of flow openings along the length of the cannula. Also, while this feature of the invention is described in connection with the preferred embodiment containing reinforced and nonreinforced sections, it is equally applicable to cannulae which are reinforced or nonreinforced over their entire length.

As such, according to one aspect of the invention, a cannula is provided in the form of a tubular body having at least a portion of its length comprised of reinforced and nonreinforced tubular sections, the nonreinforced sections including one or more openings. The relative positions of the reinforced and nonreinforced sections may be varied from those described above with respect to preferred embodiments. According to another aspect of the invention, a cannula is provided in the form of a tubular body having one or more proximal openings located between the proximal end and the midpoint of the tubular body. While the preferred embodiments of the cannulae disclosed herein include both of these aspects, it will be appreciated that the invention may be practiced by constructing a cannula that includes only one of these aspects.

The illustrated and preferred embodiments of the cannulae of the invention have a circular or substantially circular cross-section, and thus preferred sizes are provided in the form of diameters. However, it will be appreciated that any other cannula shape or configuration may be used. The openings in the nonreinforced sections of the cannulae also are described as having preferred diameters; however, noncircular openings could be used with corresponding areas determined based on (or varied from) those disclosed herein.

The cannulae 372, 372A, 372B, 404 and 404A achieve optimum fluid flow rates due to their having a minimum wall thickness and openings along the length or a portion of the length, which enhances flow through the cannula thereby allowing lower differential pressure to drive fluid flow. However, the reinforced structure of the cannulae provides sufficient structural integrity and prevents kinking and/or separation or failure at the joints between adjacent sections of the cannulae. While the reinforced sections of the cannula are preferably formed by a coated elongate member, other reinforced constructions may be used instead.

The devices and methods disclosed herein have been described in conjunction with cannulae. Nevertheless, it should be understood that the devices and methods of the invention may also be used for constructing any other hollow tubes including catheters and the like. While the above is a preferred description of the invention, various alternatives, modifications and equivalents may be used without departing from the scope of the invention. For example, the opposing sides of the coated elongate member may have an S-shape, with the reinforced section having a varying wall thickness.

Also, it should be recognized that in the embodiments of FIGS. 21–34 the cannulae have alternating reinforced sections and nonreinforced sections, wherein the nonreinforced sections include one or more openings for passing fluid. As such, the particular construction which provides the reinforced (or nonreinforced) feature may be varied without departing from the spirit and scope of the invention. The foregoing description, therefore, should not be taken as limiting the scope of the invention which is defined by the claims.

We claim:

1. A cannula for delivering fluid to or withdrawing fluid from a patient, the cannula comprising:
    a tubular body having a proximal end, a distal end, and at least one lumen;
    wherein the tubular body has at least two reinforced sections having an elongate reinforcing member, the tubular body having at least two unreinforced sections which are substantially free of any reinforcing member and include at least one opening through which fluid passes.

2. The cannula of claim 1, wherein the reinforcing member is encased in a material separate from the material forming the reinforcing member.

3. The cannula of claim 2, wherein the reinforcing member is stainless steel wire and the material comprises a polymer.

4. The cannula of claim 3, wherein the reinforcing member is configured in a helical path.

5. The cannula of claim 1, wherein the section which is substantially free of the reinforcing member comprises plain tubing sections that are completely free of any reinforcing member.

6. The cannula of claim 5, wherein the plain tubing sections comprise polyurethane.

7. The cannula of claim 1, wherein the section which is substantially free of the reinforcing member has a plurality of openings therein.

8. The cannula of claim 7, wherein the openings are disposed circumferentially about said section.

9. The cannula of claim 1, wherein the cannula is configured for use in a patient's femoral vein or artery and the tubular body has a length within a range of from about 50 to about 75 cm.

10. The cannula of claim 9, wherein the reinforced section has an inner diameter within a range of from about 16 French to about 29 French and an outer diameter within a range of from about 19 French to about 32 French.

11. The cannula of claim 10, wherein the reinforced section has an inner diameter within a range of from about 18 French to about 22 French and an outer diameter within a range of from about 21 French to about 25 French.

12. The cannula of claim 11, wherein the section which is substantially free of the reinforcing member has an inner and outer diameter which are substantially the same as the inner and outer diameter of the reinforced section.

13. A method of delivering fluid to a patient's body, the method comprising the steps of:
    providing a cannula comprising a tubular body including a proximal portion, a distal portion, a central portion disposed between the proximal and distal portions, and a lumen; wherein at least the distal portion and one of the central and proximal portions of the tubular body comprises a plurality of sections reinforced by an elongate reinforcing member encased in a material, the reinforced sections being separated by an unreinforced section which is substantially free of any reinforcing member and includes at least one opening extending into the lumen of the tubular body;
    placing at least the distal portion of the cannula into a patient's vascular system; and
    delivering fluid to the patient's vascular system by passing the fluid through the opening in the distal portion of the tubular body and the lumen, wherein the fluid is delivered to the patient's vascular system through openings in the distal portion and through openings in at least one of the proximal and central portions of the tubular body and into the lumen.

14. The method of claim 13, further comprising the step of connecting the cannula to a cardiopulmonary bypass system and delivering oxygenated blood to the patient's vascular system.

* * * * *